(12) United States Patent
Ford

(10) Patent No.: US 6,829,356 B1
(45) Date of Patent: Dec. 7, 2004

(54) SERVER-ASSISTED REGENERATION OF A STRONG SECRET FROM A WEAK SECRET

(75) Inventor: Warwick S Ford, Cambridge, MA (US)

(73) Assignee: VeriSign, Inc., Mountain View, CA (US)

( * ) Notice: Subject to any disclaimer, the term of this patent is extended or adjusted under 35 U.S.C. 154(b) by 0 days.

(21) Appl. No.: 09/574,687

(22) Filed: May 17, 2000

Related U.S. Application Data

(60) Provisional application No. 60/188,834, filed on Mar. 10, 2000, provisional application No. 60/167,453, filed on Nov. 23, 1999, and provisional application No. 60/141,571, filed on Jun. 29, 1999.

(51) Int. Cl.$^7$ .............................................. H04L 9/00
(52) U.S. Cl. ...................... 380/44; 713/171; 380/286; 380/46; 380/277
(58) Field of Search ..................... 713/171; 380/46, 380/286, 44, 277

(56) References Cited

U.S. PATENT DOCUMENTS

| | | | | |
|---|---|---|---|---|
| 5,315,658 A | * | 5/1994 | Micali | 380/286 |
| 5,623,546 A | * | 4/1997 | Hardy et al. | 713/193 |
| 5,666,414 A | * | 9/1997 | Micali | 380/286 |
| 5,850,443 A | * | 12/1998 | Van Oorschot et al. | 380/285 |
| 6,668,323 B1 | * | 12/2003 | Challener et al. | 713/183 |

OTHER PUBLICATIONS

Lomas, T.M.A.; Gong, L.; Saltzer, J.H.; and Needham, R.M.,"Reducing Risks from Poorly Chosen Keys," *Proc. 12$^{th}$ ACM Symposium on Operating System Principles*, Litchfield Park, AZ, Dec. 1989, pp. 14–18, published in *ACM Operating System Review* 23(5), pp. 14–18.

Wu, T., "The Secure Remote Password Protocol," Nov. 1, 1997, *1998 Internet Society Symposium on Network and Distributed System Security*.

Zuccherato, R., *Methods for Avoiding the "Small-Subgroup" Attacks on the Diffie-Hellman Key Agreement for S/MIME*, Internet draft, S/MIME Working Group, Jun. 1999. Retrieved from the Internet on Aug. 30, 1999:<URL:http://search.ietf.org/internet-drafts/internet-draft-ietf-smime-small-subgroup-01.txt>.

* cited by examiner

*Primary Examiner*—Gregory Morse
*Assistant Examiner*—Jacob Lipman
(74) *Attorney, Agent, or Firm*—Kenyon & Kenyon

(57) ABSTRACT

Methods for regenerating a strong secret for a user, based on input of a weak secret, such as a password, are assisted by communications exchanges with a set of independent servers. Each server holds a distinct secret value (i.e., server secret data). The strong secret is a function of the user's weak secret and of the server secret data, and a would-be attacker cannot feasibly compute the strong secret without access to both the user's weak secret and the server secret data. Any attacker has only a limited opportunity to guess the weak secret, even if he has access to all messages transmitted in the generation and regeneration processes plus a subset (but not all) of the server secret data.

120 Claims, 6 Drawing Sheets

US 6,829,356 B1

SERVER-ASSISTED REGENERATION OF A STRONG SECRET FROM A WEAK SECRET

RELATED APPLICATIONS

This application claims the benefit of U.S. Provisional Patent Application Ser. No. 60/188,834, "Server-Assisted Regeneration of a Strong Secret from a Weak Secret," by Warwick Ford, filed Mar. 10, 2000; U.S. Provisional Patent Application Ser. No. 60/167,453, "Secure Generation And Regeneration Of A Strong Secret From A Weak Secret Assisted By Multiple Servers," by Warwick Ford, filed Nov. 23, 1999; and U.S. Provisional Patent Application Ser. No. 60/141,571, "Password-Based Encryption And Recovery Protocol Immune To Password Guessing And Server Compromise," by Warwick Ford, filed Jun. 29, 1999; all of which subject matter is incorporated herein by reference.

BACKGROUND OF THE INVENTION

1. Technical Field

This invention relates generally to the secure regeneration of a user's strong secret when the user supplies a corresponding weak secret, such as a user-chosen password. For example, in computer network applications, the strong secret might be an encryption key which is used to protect the user's highly sensitive private data (such as the user's private key used in public key cryptography). In this example, the invention relates to the secure regeneration of the encryption key (and the secure recovery of the user's private key) when the user supplies his password. As another example, the strong secret might be used by the user to authenticate to a server, by demonstrating to the server the user's ability to regenerate the strong secret, without that server needing to hold data that allows the weak secret to be attacked by exhaustive trials.

2. Background Art

As a result of the continuous development of new technologies, particularly in the areas of computer networks and communications, the use of large computer networks such as the Internet is becoming more widespread. This has resulted in an increase in electronic commerce and other electronic transactions conducted over these networks. It has also resulted in increased flexibility for users, as users may increasingly access these networks from any number of locations and/or devices. The increase in electronic transactions has resulted in a corresponding increased need for security for these transactions; but the increased flexibility imposes additional requirements on security since any security measures preferably would accommodate users even as they roam across the network.

In one common scenario, the user may access the computer network from many different locations and may wish to use his private key from each location. However, at each location, he may be accessing the network from a device (hereafter referred to as a "client terminal") which cannot or does not store any data for the user, other than for transitory periods. For example, an employee might access a company's central computer network from different terminals on the company's premises, or a consumer might access the Internet from any web browser or might access a private network from a consumer kiosk. The client terminal typically can be trusted to execute its code in a trustworthy manner, to maintain the secrecy of sensitive data (e.g., the user's private key or a secret shared with an application server) during the period in which the user is actively using that terminal, and to securely destroy sensitive data when the user has finished using it. Thus, the user's private data could be securely used at the client terminal if the client terminal could somehow securely obtain a copy of the private data.

In one approach, the private data is stored on some secure hardware storage or processing token, such as a smartcard. The hardware token is physically connected to the client terminal and the private data is made accessible to the client. This approach suffers from high cost and user inconvenience since dedicated hardware is required, thus making it inappropriate for many applications.

In another approach, the private data is recovered with the assistance of other devices connected to the network (hereafter referred to as "servers"). In one example, recovery of the private data is part of the user's session login process. The user authenticates by presenting a user account name and a password subject to modest (but not extreme) guessablity controls. In particular, any party attempting a password guessing attack is limited to a small number of tries and, given this control, users can be permitted reasonably friendly password choices. Once the user is authenticated, the client terminal recovers the user's private data with the assistance of the servers.

The problem of recovering private data, such as a private key, into a stateless client terminal has been addressed in prior work through the use of a server which stores secret data for the client and facilitates the recovery process. Various protocols for using such servers, with different security and performance characteristics, were surveyed in R. Perlman and C. Kaufman, "Secure Password-Based Protocol for Downloading a Private Key," *Proc.* 1999 *Network and Distributed System Security Symposium*, Internet Society, January 1999. The protocols described in that work are primarily variants or derivatives of Bellovin and Merritt's EKE protocol (e.g., see S. Bellovin and M. Merritt, "Encrypted Key Exchange: Password-based protocols secure against dictionary attacks," *Proc. IEEE Symposium on Research in Security and Privacy*, May 1992; and S. Bellovin and M. Merritt, "Augmented Encrypted Key Exchange: a password-based protocol secure against dictionary attacks and password file compromise," *ATT Labs Technical Report*, 1994) and Jablon's SPEKE protocol (e.g., see D. Jablon, "Strong password-only authenticated key exchange," *ACM Computer Communications Review*, October 1996; and D. Jablon, "Extended Password Protocols Immune to Dictionary Attack," *Proc. of the WETICE '97 Enterprise Security Workshop*, June 1997. Related patents include U.S. Pat. No. 5,241,599 ("Cryptographic protocol for secure communications" by Bellovin and Merritt) and U.S. Pat. No. 5,440,635 ("Cryptographic protocol for remote authentication" by Bellovin and Merritt). Other related server-assisted secret recovery protocols have been proposed by Gong, et al. (e.g., L. Gong, T. M. A. Lomas, R. M. Needham, and J. H. Salzer, "Protecting Poorly Chosen Secrets from Guessing Attacks," *IEEE Journal on Selected Areas in Communications*, vol.11, no.5, June 1993, pp. 648–656; L. Gong, "Optimal Authentication Protocols Resistant to Password Guessing Attacks," *Proc. 8th IEEE Computer Security Foundations Workshop*, Ireland, Jun. 13, 1995, pp. 24–29; and L. Gong, "Increasing Availability and Security of an Authentication Service," IEEE Journal on Selected Areas in Communications, vol. 11, no. 5, June 1993, pp. 657–662); by Wu (e.g., T. Wu, "The Secure Remote Password Protocol," *Proc.* 1998 *Network and Distributed System Security Symposium*, Internet Society, January 1998, pp. 97–111), and by Halevi and Krawcyzk (e.g., S. Halevi and H. Krawczyk, "Public-key cryptography and password protocols. Public-key cryptography and password protocols," *Proceedings of the Fifth ACM Conference on Computer and Communications Security*, 1998).

However, all of the above methods suffer from a significant shortcoming. The server represents a major vulnerability. If a server operator, or someone who compromises a server, wishes to determine a user's password or private data (either of which will generally enable the attacker to masquerade as the user), viable attacks are possible, despite aspects of some approaches that minimize the sensitivity of the data stored on the server. For example, in certain of the work mentioned above, the server does not store the user's password but instead stores a value computed as a one-way function of the password. Anyone learning that value might be able to determine the password by exhaustively applying the one-way function to guessed passwords and comparing the result with the stored value. In general terms, the previously mentioned approaches suffer from the weakness that anyone who can access the server database or can disable any throttling or lockout mechanism on the server can try passwords exhaustively until a user's account on the server is penetrated.

In some application scenarios the above weakness can significantly undermine the attractiveness of the server-assisted approach to recovery of private data. For example, the above attack scenario significantly hampers the non-repudiation properties otherwise inherent in digital signature technology. If a roaming user digitally signs a transaction using the user's private key from a client terminal and later wishes to deny the user's digital signature, the user can plausibly claim that the server operator or someone who compromised the server obtained the user's private key as described above and digitally signed the transaction posing as the user. Risks and liability faced by a server operator are reduced if it can justifiably counter claims from users that it, or its personnel, may have masqueraded as the user.

Thus there is a need for an approach that permits a client terminal to recover a user's private data with the assistance of servers while remaining resistant to attacks on the servers. More generally, the problem of recovering private data into a stateless client can be reduced to the problem of generating and regenerating strong secret data for a user from the user's weak secret data, such as a password. The strong secret can be used as an encryption key in a symmetric cryptosystem to encrypt and recover any amount of private data that might be held in an encrypted form in a widely accessible storage place.

There is also a need for approaches which permit a user to authenticate to an application server from a stateless client terminal on the basis of a presented password. Current approaches, such as the Kerberos authentication method (e.g., see J. T. Kohl and B. C. Neuman, *The Kerberos Network Authentication Service (V5)*, Request for Comments (RFC) 1510, Internet Activities Board, 1993), involve the user authenticating first to an authentication server and subsequently to an application server using a cryptographic "ticket" from the authentication server. However, these approaches suffer from the shortcoming that either the application server or an authentication server holds data which, if exposed to an attacker (either internal or external to the organization that operates the server), allows the attacker to exhaustively guess passwords and likely determine the user's password. These problems may be averted if the user authentication is based on a user presenting evidence of knowledge of strong secret data rather than weak secret data to the application server or authentication server.

There is also a need for approaches which allow a user to create a digital signature from a stateless client terminal into which a password is entered. One approach to satisfying this requirement is to recover the user's private key into the terminal as outlined above and to compute the digital signature in the client terminal. Another approach for satisfying the requirement, which does not require the private key to be assembled in one place, involves communications with multiple servers each of which holds an independent part of the user's signing private key. Such servers each generate part of the digital signature and the parts are combined in the client terminal to give the full digital signature. While relevant other work on such methods achieves the goal of not assembling the private key in one place, such work suffers from the weakness that one or more servers that participate in the signing process hold data that allows the user's password to be exhaustively attacked. Consequently, there is a risk that anyone who compromises any one such server can determine the user's password by exhaustive guessing, which, if successful, allows the attacker to forge digital signatures purporting to be from that user. The problem can be averted by authenticating to the servers that generate parts of the digital signature by demonstrating knowledge of a strong user secret, which may have been regenerated on the basis of presentation of a weak user secret, rather than by authenticating directly on the basis of the weak user secret itself.

Thus, there is a need for an approach that permits a client terminal to regenerate a user's strong secret data from weak secret data with the assistance of servers while remaining resistant to attacks on the servers.

DISCLOSURE OF INVENTION

In accordance with the present invention, a method for establishing (300,500) a user's (100) strong secret data to allow subsequent recovery (400,600) of the strong secret data, includes the following steps. Weak secret data, for example a password, is determined (320) for the user (110). The user authenticates (310) to servers (130), which include secret holding servers (preferably at least two secret holding servers). Each secret holding server has corresponding server secret data. A generating client (120), possibly assisted by the secret holding servers (130), computes (330, 530) the user's strong secret data. The strong secret data is a function of the user's weak secret data and of the server secret data. In a preferred embodiment, secret components are computed (534) for each secret holding server. Each secret component is a function of the weak secret data and of the strong secret data for that secret holding server. The secret components are combined (536) to generate the strong secret data. The generating client (120) also determines (350) verifier data for verification servers (130), preferably at least two. The verifier data enables a verification server (130) to verify (402,602) whether a device (220) has subsequently successfully recovered (400,600) the strong secret data. However, it is computationally infeasible for the server (130) to determine the weak secret data based only on access to its verifier data. The verification servers (130) may store (355) the verifier data for subsequent use. The generating client (120) may additionally use the strong secret data as a cryptographic key in a symmetric cryptosystem to encrypt (370) other private data for the user (110), such a the user's private key.

In a preferred embodiment, the strong secret data is computed (330,530) as follows. The generating client (120) computes server request data for at least one of the secret holding servers (130). The server request data is a function of the weak secret data and of an ephemeral client secret, but the server request data does not reveal information about the weak secret data without knowledge of the ephemeral client secret. As a result, the generating client (120) can transmit the server request data to the secret holding server (130) without compromising the weak secret data. The secret holding server (130) computes server response data, which is a function of the server secret data for the secret holding server and of the received server request data. The server response data does not reveal information about the server secret data without knowledge of the weak secret data and the ephemeral client secret. As a result, the secret holding server (130) can transmit the server response data to the generating client (120) without compromising its server secret data. The generating client (120) computes a secret component for the secret holding server as a function of the server response data received from the secret holding server and of the ephemeral client secret. The secret component is a function of the weak secret data and of the server secret data but is independent of the ephemeral client secret. The generating client (120) then computes the user's strong secret data as a function of the secret components.

In a further refinement, the weak secret data is a password PWD and the server secret data are random integers b(i), where i is an index for the servers (130). The generating client (120) computes (534) server request data which includes the value $M=w^a$. Here, w=f(weak secret data), where f is a function which generates an element of a group G, and the ephemeral client secret includes the random integer a for which there exists a corresponding integer a' such that $x^{aa'}=x$ for all x in the group G. The group G is a finite group in which exponentiation is efficient but the discrete logarithm problem is computationally infeasible, for example the multiplicative group of the set of integers modulo a prime p or a group of points on an elliptic curve over a finite field. All exponentiations are calculated in the group G. The secret holding server (130) computes (534) server response data which includes the value $c(i)=M^{b(i)}$. The generating client (120) then computes (534) secret components according to $K(i)=h(c(i)^{a'})$ wherein h is a function. The user's strong secret data is then computed (536) as a function of all the secret components K(i), for example as the exclusive-OR of these components.

In another aspect of the invention, the strong secret data is recovered (400,600) from the weak secret data as follows. A recovery client (220) receives (410) the user's weak secret data. The recovery client (220) then computes (440,640) the user's strong secret data, which is a function of the user's weak secret data and of server secret data for at least two secret holding servers (130). In a preferred embodiment, the computation is based on secret components, as described above. The recovery client (220) also determines (450,650) proof data for proving (460,660) that the strong secret data was successfully computed (401,601) and transmits (455, 655) the proof data to verification servers (130), which may or may not also be secret holding servers. By validating the proof data using the corresponding verifier data, the verification servers (130) may determine (460,660) whether the strong secret data was successfully recovered (401,601) and take appropriate actions (680). For example, if it seems likely that an entity (220) which does not have access to the weak secret data is attempting to regenerate (401,601) the strong secret data, then the verification server might instruct the secret holding servers (130) to stop participating in any further recovery attempts (400,600). Alternately, the verification server might be responsible for generating part of a digital signature on behalf of user (110). In this case, the proof data might be accompanied by a message digest of a message to be signed and the verification server (130) will generate its part of the digital signature only when simultaneously presented with adequate proof data. If additional private data was encrypted (370) using the strong secret data as a cryptographic key, then the recovery client (220) may additionally decrypt (470) the private data.

In a preferred embodiment, the strong secret data is computed (440,640) as follows. The recovery client (220) computes (420,620) server request data for at least one and preferably more than one secret holding server. The server request data is a function of the weak secret data and of an ephemeral client secret, but it does not reveal significant information about the weak secret data without knowledge of the ephemeral client secret. The server request data is transmitted (425,625) to the secret holding server, which calculates (430,630) server response data based on the server request data and its server secret data. The server response data does not reveal significant information about the server secret data without knowledge of the server request data. The server response data is transmitted (435,635) to the recovery client (220), which recovers (440,640) the user's strong secret data using the server response data.

In a preferred embodiment corresponding to the one described above, the recovery client (220) randomly generates (624) an ephemeral client secret a, which is an integer for which there exists a corresponding integer a' such that $x^{aa'}=x$ for all x in group G. It computes (626) server request data including the value $M=w^a$ where w=J(PWD) as above and transmits (625) this data to at least one secret holding server (130). Each secret holding server (130) computes (630) server response data including the value $c(i)=M^{b(i)}$ and transmits (635) this back to the recovery client (220). The recovery client (220) computes (644) the secret components $K(i)=h(c(i)^{a'})$ where h is the same function as above. The secret components are then combined (646), as in the generating client (120), to recover the strong secret data.

These methods (300,400,500,600) are advantageous because they allow a user (110) to recover (400,600) strong secret data from weak secret data at many recovery clients (220). The methods are generally resistant to attacks, including attacks on or compromise of the servers (130). In further accordance with the invention, software and/or hardware (100,200) implements the above methods.

BRIEF DESCRIPTION OF THE DRAWINGS

These and other more detailed and specific objects and features of the present invention are more fully disclosed in the following specification, reference being had to the accompanying drawings, in which.

DETAILED DESCRIPTION OF THE PREFERRED EMBODIMENTS

Figure 1:
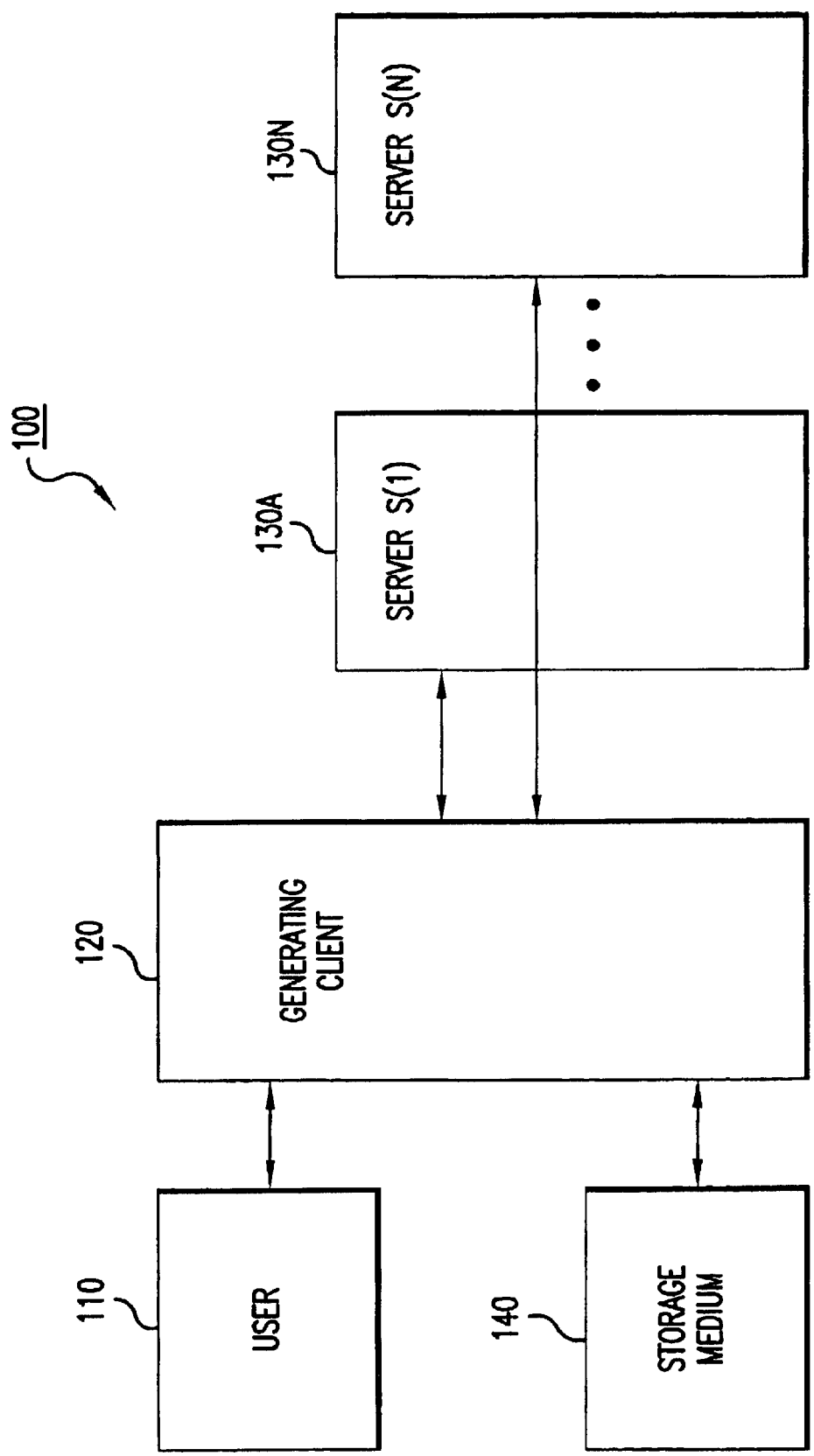
FIG. 1 is a block diagram of an initializing system (100) according to the present invention.
Figure 2:
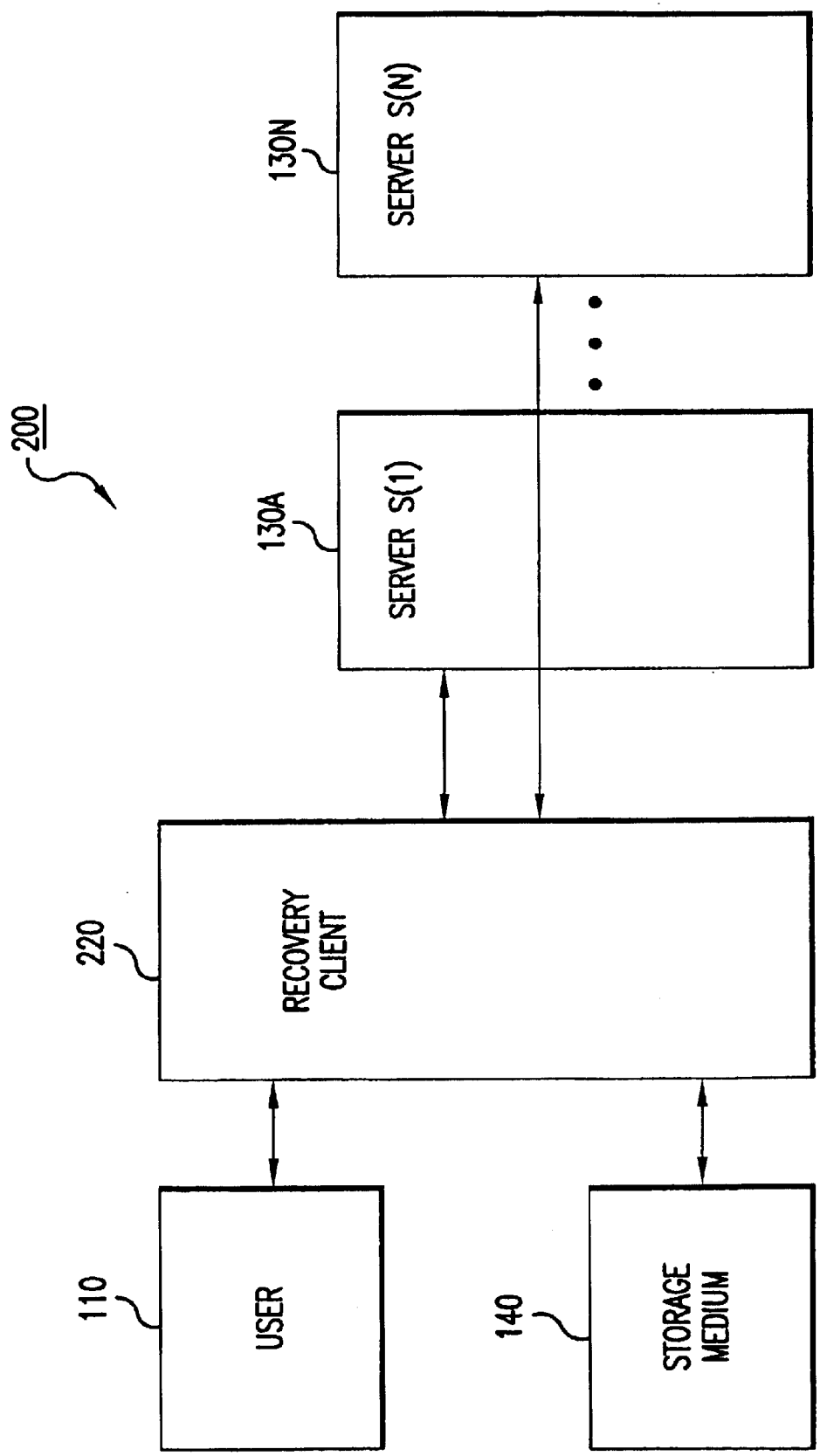
FIG. 2 is a block diagram of a recovery system (200) according to the present invention.

FIGS. 1 and 2 are block diagrams illustrating systems 100 and 200 in accordance with the present invention. For reasons which shall be apparent below, system 100 shall be referred to as an "initializing system" and system 200 as a "recovery system."

Initializing system 100 includes a user 110, a client terminal 120, a number of servers 130A–130N (collectively, servers 130) and optionally also a storage medium 140. The user 110 may be an individual, a group of individuals, a legal entity such as a corporation, a computer, or the like. Client terminal 120, which shall be referred to as the "generating client" 120, is typically some type of computer-based device. Examples include personal computers, computer workstations, and digital wireless phones. Servers 130 typically are also computer-based devices. In this description, they are referred to as "servers" because of the role that they play but this terminology is not meant to imply that they are necessarily server-class computers. At least one and possibly all servers 130 are secret holding servers. The role played by secret holding servers will be described more fully below. In certain embodiments, there may be a single server 130. Alternate embodiments prefer two or more secret holding servers 130. In embodiments which utilize multiple secret holding servers 130, the secret holding servers preferably are controlled by different entities so that no individual entity has access to all of the secret holding servers 130, for reasons discussed below. Examples of storage medium 140 include a network disk drive, a directory service, or a file server. The user 110, servers 130, and storage medium 140 are each coupled to the generating client 120. The connections may be made by any number of means, including over computer networks such as the Internet or by wireless connections. The connections need not be permanent or persistent. In fact, as will be described further below, generating client 120 performs a particular task and once that task is completed, there is no need for the other components to communicate further with generating client 120.

Recovery system 200 is similar to initializing system 100, except that generating client 120 is replaced by another client terminal 220, which shall be referred to as the recovery client 220. Recovery client 220 may or may not be the same physical device as generating client 120. Examples of recovery clients 220 include personal computers, digital kiosks, digital wireless phones or other wireless devices, and smartcards.

Systems 100 and 200 implement the following functionality. User 110 has strong secret data which he would like to be able to use from recovery client 220, where "strong" implies data that cannot feasibly be deduced by exhaustive guessing and "secret" means data that nobody other than the secret holder (e.g., the user in the case of the user's strong secret data) should feasibly be able to determine. However, recovery client 220 is a client terminal which cannot or does not have access to user 110's strong secret data a priori. Furthermore, user 110 does not directly know his strong secret data so, for example, user 110 cannot simply input his strong secret data into the recovery client 220. Hence, recovery client 220 must somehow regenerate or recover user 110's strong secret data and it must do so in a secure fashion in order to maintain the strong secrecy of the data. User 110 knows certain weak secret data, where "weak" implies that the data can be correctly guessed within a moderate number of tries. For example, it may be a user-specified password. User 110 enters his weak secret data into recovery client 220 and, based on user 110's weak secret data, system 200 then securely recovers the strong secret data, thus permitting user 110 to use his strong secret data from recovery client 220. System 100 and generating client 120 perform various initialization steps based on the strong secret data and the weak secret data, so that system 200 and recovery client 220 may later securely recover the strong secret data from the user 110's weak secret data. Servers 130 assist in these processes.

In a preferred embodiment, the strong secret data is a cryptographic key which is used in a symmetric cryptosystem to encrypt user 110's private data which might include a private key, and the weak secret data is a password. The encrypted private data are stored in storage medium 140. When user 110 desires to use his private data from recovery client 220, he supplies his password to recovery client 220. The recovery client 220 then recovers the cryptographic key which is used to decrypt the user's encrypted private data. User 110 can then use his private data as desired, for example, by using his private key to digitally sign messages within recovery client 220.

Figure 3:
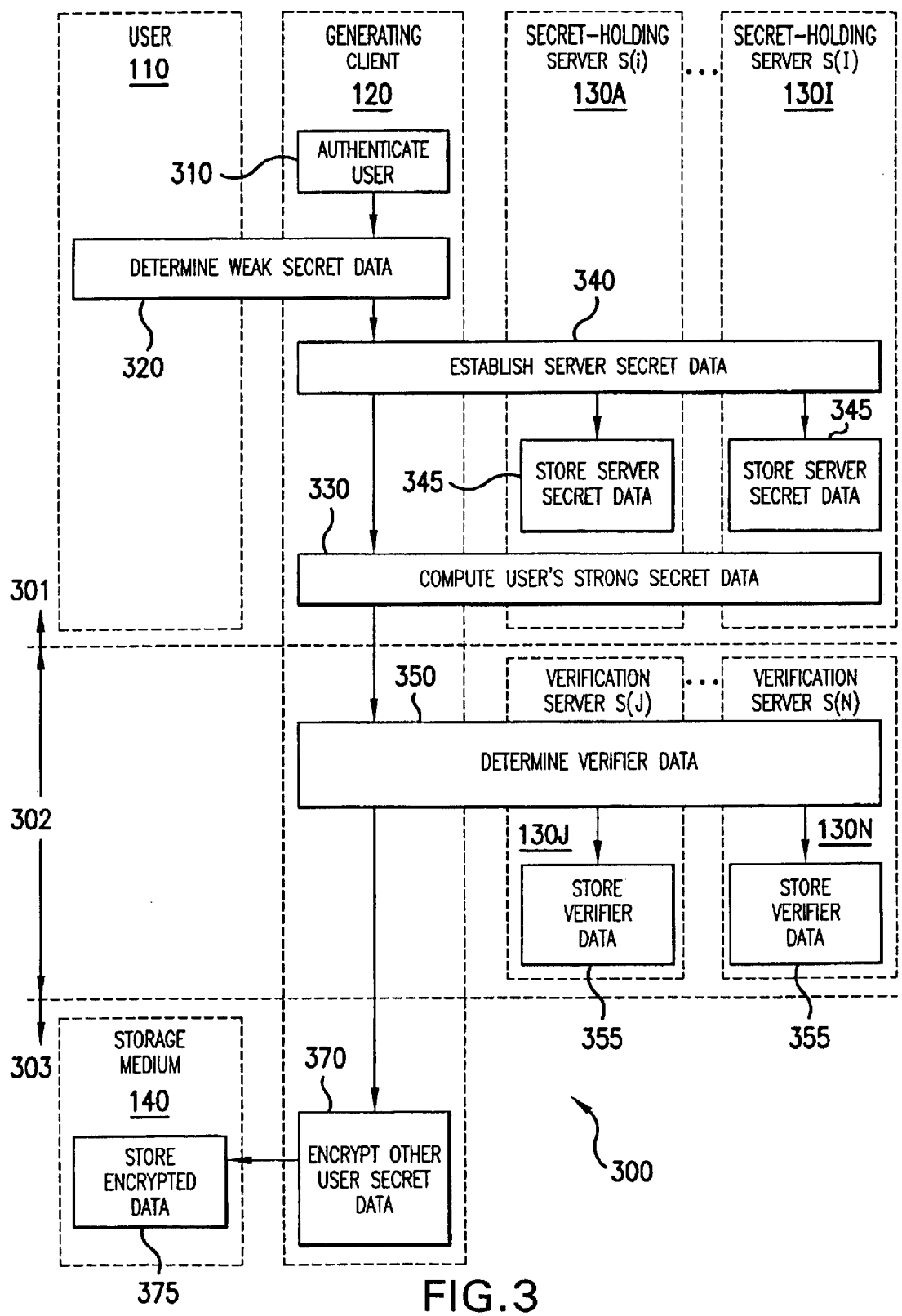
FIG. 3 is an event trace illustrating an example method (300) for initializing system 100, according to the present invention.
Figure 4:
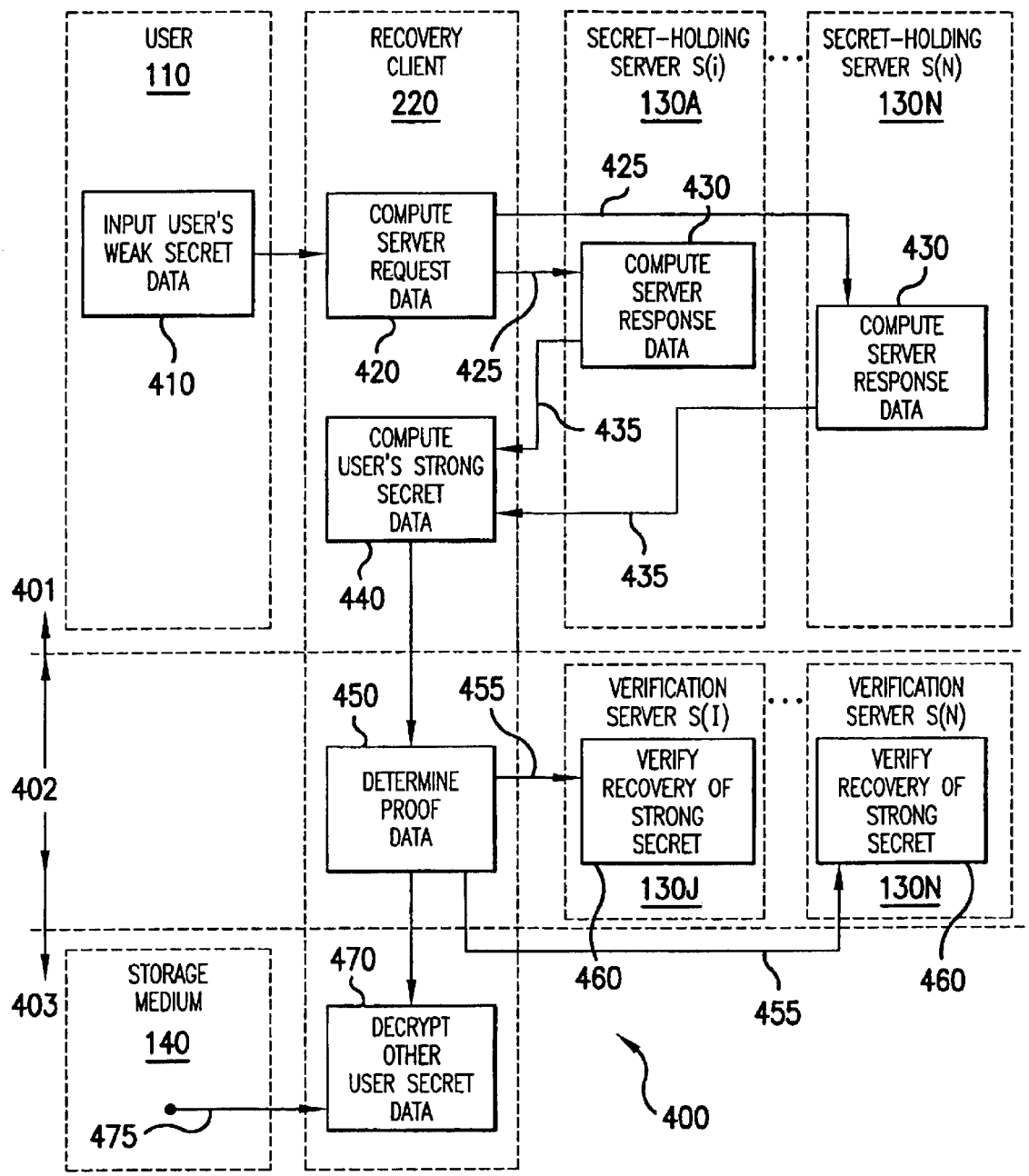
FIG. 4 is an event trace illustrating an example method (400) for recovering strong secret data which has been initialized using method 300.

FIGS. 3 and 4 are event traces which illustrate example methods 300 and 400 for performing initialization of system 100 and for recovering the strong secret data from user 110's weak secret data, respectively. Method 300 uses system 100 and method 400 uses system 200. Each of the dashed boxes 110, 120, 130, 140, and 220 represents one of the components of system 100 or system 200. The solid boxes represent various steps in the two methods 300 and 400. The location of a solid box within a dashed box generally indicates that that specific step is performed by that specific component. For example, in FIG. 4, step 310 is located within the dashed box for generating client 120. This generally indicates that generating client 120 performs step 310. The methods preferably are implemented by software running on the various components within each system, possibly assisted by hardware modules, but the processing modules depicted in FIGS. 3 and 4 can also be implemented in hardware and/or firmware.

Referring first to FIG. 3, initializing method 300 may be broken down into three general stages 301–303. In the generation stage 301, system 100 determines the user's strong secret data, which in this embodiment shall be referred to as K. This stage 301 includes steps which allow system 200 to later securely regenerate strong secret K. In the verifier setup stage 302, system 100 executes steps which allow system 200 to verify the subsequent successful recovery of strong secret K. In the storage stage 303, system 100 uses the strong secret K to encrypt private data for the user (e.g., the user's private key or digital certificate), for later recovery by recovery client 220. Not all implementations will utilize all stages 301–303, but they are included in this example to illustrate various aspects of the invention.

In the generation stage 301, the generating client 120 begins by authenticating 310 the user 110 as a legitimate user for user account U. This might involve communications with other systems, such as an authentication server.

The user 110 and/or generating client 120 determines 320 the user 110's weak secret data, referred to here as PWD. The weak secret is typically a user password in this embodiment, and this description will characterize it as such. However, the weak secret could take other forms and/or be wholly or partially from another source, such as biometric signature data and/or data stored in a physical token or device associated with the user 110. In FIG. 3, generation 320 of the weak secret is shown as covering both the user 110 and generating client 120. This is because either may participate to various degrees, depending on the specific implementation. For example, in one approach, the user 110 proposes a password PWD and the generating client 120 either accepts or rejects the password, depending on whether it meets certain anti-guessing criteria. In a different approach, the generating client 120 generates the password PWD (for example, using a random process) and then assigns it to the user 110. In any event, at the end of step 320, both the user 110 and generating client 120 have access to the password PWD.

Server secret data b(i) for user 110 is established 340 for some and perhaps all of the servers S(i), where i is an index for the servers. The servers 130 for which server secret data is established are referred to as secret holding servers. Analogous to step 320, step 340 is shown as covering the generating client 120 and the secret holding servers S(i) because each may participate to various degrees, depending on the specific implementation, as will be described further below. If a specific implementation calls for the generating client 120 and secret holding servers S(i) to exchange messages in order to establish 340 the server secret data, it is important that these messages be integrity protected and the source of each message be authenticated in order to maintain the security of the overall protocol. For example, the generating client and secret holding servers S(i) might exchange messages over a secure channel. At the end of step 340, each secret holding server S(i) has access to its corresponding server secret data b(i) and typically will also securely store 345 it for future use in recovering the user's strong secret data. The generating client 120 may also have access to the server secret data b(i), depending on the specific implementation. However, in this case, it typically would use the server secret data b(i) only as part of the initialization 300 and then would erase it. The generating client 120 does not retain the server secret data b(i) for future use.

The generating client 120 computes 330 the user's strong secret data K. The strong secret data K is a function of the user's weak secret PWD and of the server secret data b(i). Again, step 330 covers both the generating client 120 and the servers S(i) because, depending on the implementation, each may contribute to the calculation required to convert the user's weak secret PWD and the server secret data b(i) into the strong secret K. However, although the secret holding servers S(i) may calculate intermediate values, only the generating client 120 has access to the final strong secret K.

In the verifier setup stage 302, verifier data v(i) is determined 350 for some and perhaps all of the servers S(i) and preferably is also stored 355 by each server S(i). The servers for which verifier data is established shall be referred to as verification servers 130. The verifier data v(i) enables the verification servers S(i) to verify whether a recovery client 220 has successfully recovered the user's strong secret data. In a preferred embodiment, the secret holding servers are also the verification servers, although this is not necessarily the case. Alternately, the verification servers may be physically distinct from the secret holding servers, but there may be one verification server corresponding to each secret holding server. For redundancy purposes, it is preferable to have at least two verification servers. The verifier data is selected such that it is computationally infeasible for the verification server to determine the weak secret data based only on access to its verifier data. In one approach, the generating client 120 determines 350 the verifier data, which is then transmitted to server 130. In an alternate approach, each server 130 determines its own verifier data. Analogous to step 340, if a specific implementation calls for the generating client 120 and server 130 to exchange messages in order to determine 350 the verifier data, it is important that these messages be integrity protected and the source of each message be authenticated.

In the storage stage 303, the generating client 120 additionally encrypts 370 other data for the user, which shall be referred to as the user's private data. In a preferred embodiment, the strong secret data K is used as a cryptographic key in a symmetric cryptosystem. For example, the private data could be the user's private key, a secret shared by the user and an application server, the user's credit card account numbers or other private or secret data which the user would like to use from the recovery client 220. The encrypted private data EPD is stored 375 in storage medium 140 for later recovery. Storage medium 140 typically is widely accessible; the user's private data is secured because it is stored in encrypted form. In alternate embodiments, the strong secret data K may be used in other ways to securely store the user's private data.

Referring now to FIG. 4, the recovery method 400 may also be broken down into three general stages 401–403 corresponding to stages 301–303 of method 300, not all of which are required in all implementations. In stage 401, the recovery client 220 recovers the user's strong secret K, with the assistance of the secret holding servers 130. In stage 402, one or more verification servers 130 determine whether the recovery client 220 has successfully recovered the strong secret data K. In stage 403, the recovery client 220 also recovers the user's private data stored in storage medium 140. Again, the example method 400 is selected in order to illustrate various aspects of the invention, not all of which are required to practice the invention.

The recovery client 220 recovers 401 the user 110's strong secret data as follows. The user 110 inputs 410 his user account identifier U and weak secret data PWD to the recovery client 220. The recovery client 220 computes 420 server request data for each of the secret holding servers S(i) and transmits 425 the server request data to the secret holding servers. The server request data is a function of the weak secret data PWD and an ephemeral client secret a, such that the output of the function does not reveal information about the weak secret to a party that does not know the ephemeral client secret a. In response to the received server request data, each secret holding server S(i) computes 430 server response data, which is a function of the server request data and of the server's secret data b(i), and transmits 435 the server response data back to the recovery client 220. The recovery client 220 then computes 440 the user's strong secret data K as a function of the received server response data. As described previously, the strong secret data is a function of the user's weak secret data and of the server secret data. The recovery client 220 has direct access to the user's weak secret data but does not have direct access to the server secret data. However, the server response data contains a dependency on the server secret data; so the recovery client 220 has indirect access to the server secret data and can recover the user's strong secret data without requiring direct access to the server secret data.

In recovery stage 403, recovery client 220 retrieves 475 the user's encrypted private data EPD and decrypts 470 it using the recovered strong secret data K. In this way, recovery client 220 also recovers the user's private data, such as the user's private key.

At the end of the period of legitimate use of strong secret K and any other recovered private data (e.g., at the end of the user's on-line session using the recovery client 220), the copy of K and the other recovered private data in the recovery client 220 preferably are destroyed.

In the verification stage 402, the recovery client 220 determines 450 proof data d(i) for proving to at least one verification server (preferably to at least two one verification servers) that the strong secret data was successfully recovered by the recovery client 220. The proof data d(i) is transmitted 455 to each of the verification servers. Each verification server can then verify 460 whether this particular instantiation of the regeneration process 400 successfully recovered the user's strong secret data K and can take appropriate actions. For example, in one embodiment, a verification server 130 might be responsible for a portion of the process of generating a digital signature on behalf of the user 110. In this case, the proof data may be accompanied by a message digest of the user-originated message to be digitally signed. Upon verification of the proof data, the verification server 130 generates its component of the digital signature and transmits this back to the client. The client determines the full digital signature based on the components which it receives.

As another example, the verification server may also be a secret holding server. This server might determine, based on the history of past unsuccessful attempts, that an entity which does not know the weak secret data is attempting to regenerate the strong secret data. Accordingly, the secret holding server may refuse to participate in further recovery attempts or take other actions. In one approach, the secret holding servers keep track of all attempts to regenerate the strong secret data K for each user account and, in the event of excessive failed attempts for any account, will throttle and/or lock out further regeneration attempts on that account until either the password is changed or a local administrator determines that the failed attempts do not represent a threat to the account.

Different types of verification may be used. In one approach which uses static verifier data, the verifier data v(i) is a one-way function of one or more data items that include the strong secret data K. The verifier data is computed by the generating client 120 or some other trusted party and is sent to and stored at each verification server as part of the initializing process 300. Preferably, different verifier data is computed for each verification server 130, for example, by applying a hash function to a data string comprising the strong secret data K concatenated with a unique but non-secret identifier for the particular server 130. In verification stage 402, the recovery client 220 computes 450 the proof data by recomputing the same one-way function of the regenerated strong secret data. If the proof data computed by the recovery client 220 matches the verifier data stored by the server, then recovery of the strong secret data is verified.

In one variant of this approach, the recovery client 220 first recomputes verifier data as a one-way function of the strong secret K then computes the proof data as a one way function of one or more data items that include the recomputed verifier data and a non-secret nonce, such as a timestamp or a nonce sent previously from the server to the recovery client either along with the server response data (e.g., in the case of a secret holding server) or in a separate message. The verification server 130 computes its own proof data by applying the same one-way function to its copy of the verifier data and the nonce. If the proof data computed by the recovery client 220 matches the proof data computed by the verification server 130, then recovery of the strong secret data is verified. The nonce allows the server to confirm that the proof data is fresh and is not a replay of earlier proof data for the same user. In other words, the nonce distinguishes the current proof data from other instances of proof data for the same user.

In a different verification approach, assume that the user's private data stored in storage medium 140 includes private data (e.g., a private key) of an asymmetric proof system, for which there exists corresponding public data. The asymmetric proof system has the property that an entity which has access to the private data can prove it has access to the private data to a second entity with access to the public data without disclosing the private data to the second entity. The asymmetric proof system could be a digital signature system, such as RSA or DSA, a zero-knowledge proof system whereby possession of information can be verified without any part of that information being revealed, or another type of asymmetric proof system. For the purposes of describing the invention, a digital signature system will be assumed. In this case, the recovery client 220 may generate proof data which depends on the decrypted private data, thus proving successful recovery of the private data and, hence, also successful recovery of the strong secret data (since the strong secret data is required to successfully decrypt the private data).

For example, if the private data is the user's private digital signature key, the proof data could comprise a message, preferably containing a nonce to allow detection of replays, which was digitally signed using the private key. If the verifier data is the corresponding public key, it could then be used to verify successful recovery of the private key. Verifying 460 successful recovery of the strong secret data would then include verifying that the private key was used to digitally sign the message. If a nonce is used, then verifying the freshness of the proof data would involve verifying that the digitally signed message contains the nonce. As an alternative, the proof data may be a function of other user data which the verification server can authenticate as originating from the user. Other variations of the verification step may be based on other approaches, for example using zero-knowledge proofs (e.g., see J. Nechvatal, "Public Key Cryptography," in G. J. Simmons (Ed.), *Contemporary Cryptology: The Science of Information Integrity* (New York: IEEE Press, 1992), pp. 107–126).

Other variations of methods 300 and 400 will be apparent. However, in order to maintain resistance against attacks, including compromise of the servers, any successful protocol preferably should include the following attributes. First, observation of any or all messages by an eavesdropper cannot yield sufficient information for the eavesdropper to feasibly deduce either the weak secret data PWD or the strong secret data K. Second, knowledge of anything less than all of the server secret data from a predetermined number of secret holding servers will not permit any party to feasibly deduce either the weak secret data PWD or the strong secret data K. "Any party" includes the servers themselves. That is, a server cannot feasibly deduce either weak secret data PWD or the strong secret data K unless a predetermined number of secret holding servers collude by either disclosing their server secret data or by failing to throttle or lock out the account in the event of excessive failed attempts at executing the protocol. As a result, methods 300 and 400 are advantageous because they are resistant to many types of attacks, including compromise of a server, when the strong secret data depends on server secret data of at least two secret holding servers.

Figure 5:
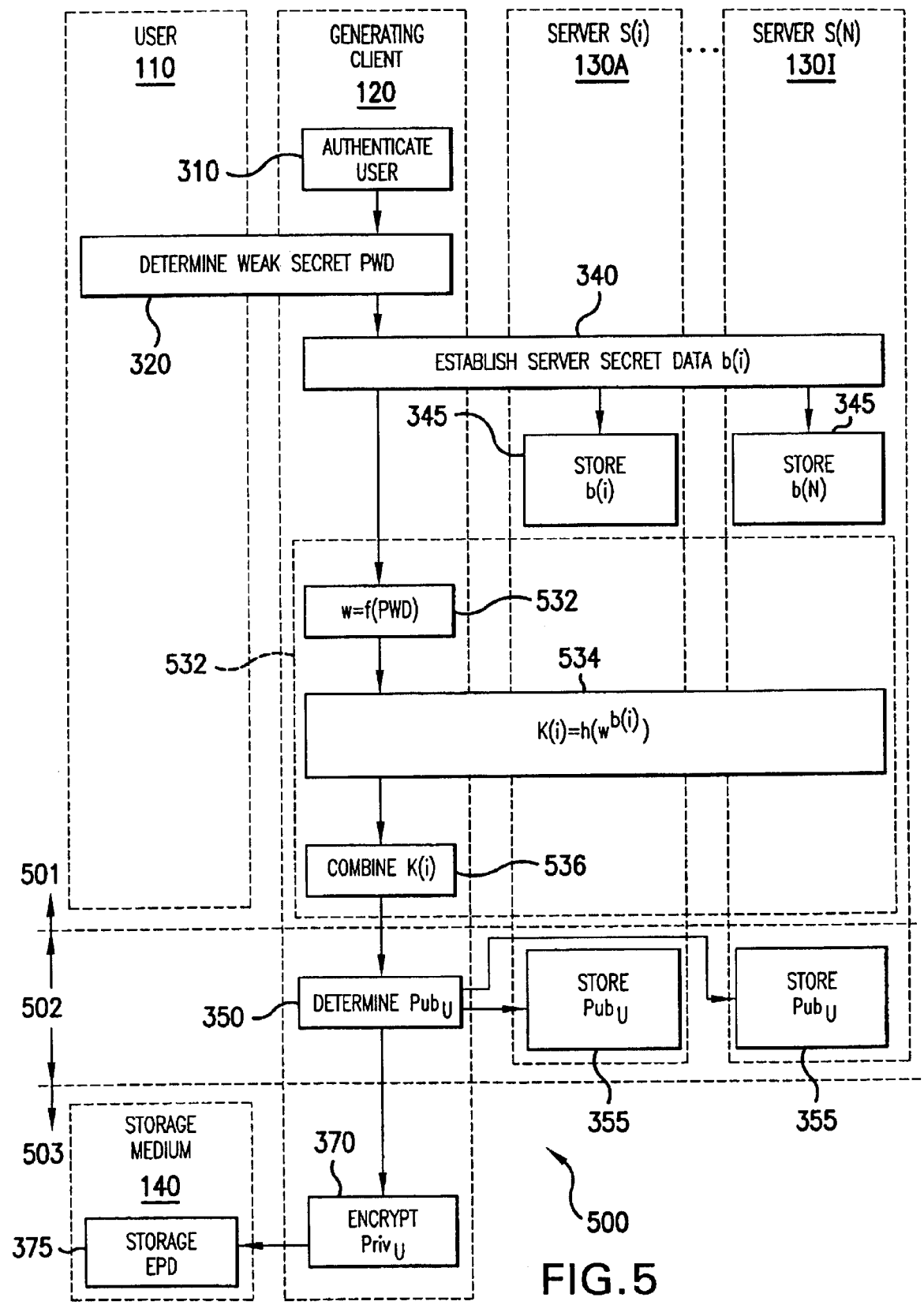
FIG. 5 is an event trace illustrating a preferred method (500) for initializing system 100 using exponentiation in a group G, according to the present invention.
Figure 6:
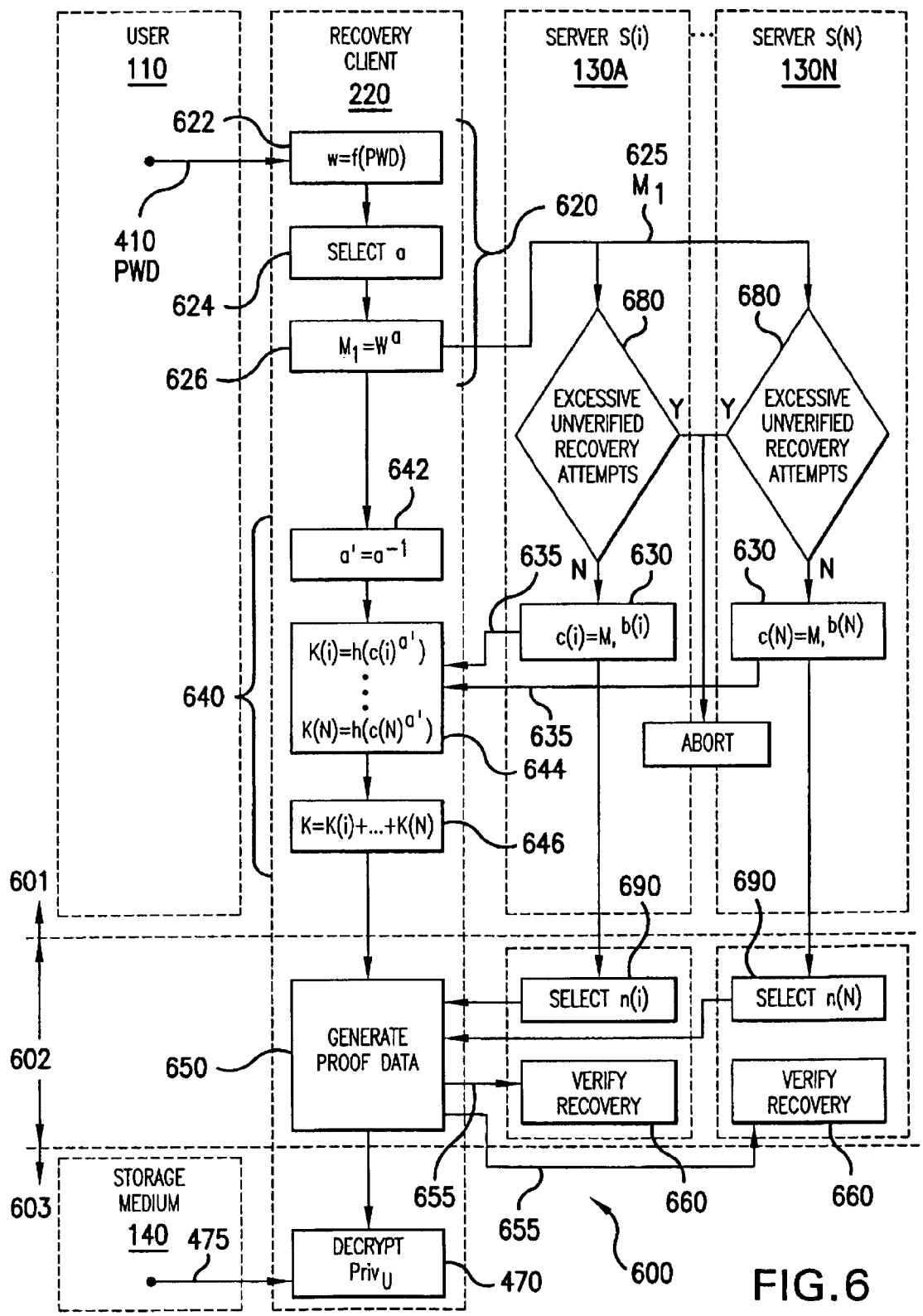
FIG. 6 is an event trace illustrating a preferred method (600) for recovering strong secret data which has been initialized using method 500.

FIGS. 5 and 6 are event traces which illustrate preferred embodiments 500 and 600 of methods 300 and 400, respectively. The preferred embodiments are based on computations within a finite group G in which exponentiation is efficient but the discrete logarithm problem is computationally infeasible. A suitable group G is the multiplicative group of the set of integers modulo a prime p, where p is a large prime with properties that make it suitable as a Diffie- Hellman modulus. In particular, at a minimum, p−1 must have a large prime factor. A better restriction on p is that it be a safe prime p=2q+1, where q is prime. Other cyclic groups are also suitable, including a group of points on an elliptic curve over a finite field. The methods will be illustrated in the context where the strong secret data K is subsequently used as a cryptographic key used to encrypt the user's private key but, as discussed previously with methods 300 and 400, preferred methods 500 and 600 also are not limited to this particular application. In this particular example, each server 130 functions as both a secret holding server and as a verification server.

Referring first to FIG. 5, initializing method 500 may be broken down into the three general stages 501–503, analogous to stages 301–303 of method 300. The generation stage 501 begins the same as generation stage 301. The generating client 120 authenticates 310 the user as a legitimate user for account U. Next, the user's weak secret data PWD is determined 320.

Server secret data b(i) for user 110 is established 340 for each secret holding server S(i), where i is an index for the servers 130. In this embodiment, the server secret data is a random integer b(i), preferably an even number to prevent against small subgroup attacks that are well-known in Diffie-Hellman methods. At the end of step 340, each secret holding server has access to its server secret data b(i); the generating client 120 may or may not have access to the server secret data b(i), depending on the specific implementation. In one approach in which both a secret holding server S(i) and the generating client 120 have access to that server's server secret data b(i), the server secret data b(i) is generated by either the generating client 120 or by the server S(i) and communicated to the other party in an encrypted form. Alternately, the server secret data is computed by combining random values from both the generating client 120 and secret holding server S(i), for example, by Diffie-Hellman key exchange. Communications preferably are protected such that no other party can learn b(i). On the other hand, if the generating client 120 does not have access to the server secret data b(i), then each secret holding server S(i) might generate its server secret data b(i) but does not share it with the generating client 120 or the other servers S(i). Whatever the generation method, each server typically will securely store 345 its server secret data for future use in regenerating the user's strong secret data.

The generating client 120 computes 530 the strong secret data K as follows. First, the generating client 120 computes 532 w=f(PWD), where f is a one-way function generating an element of group G. Next, a secret component K(i) is computed 534 for each secret holding server according to the relationship $K(i)=h(w^{b(i)})$. In this expression, h is a one-way function, such as a cryptographic hash function, which generates a value with suitably unbiased and uncorrelated bits, as might be suitable for use as a symmetric encryption key. The exponentiation $w^{b(i)}$ is computed in the group G (i.e., integers modulo p in this example). Depending on the implementation, the secret holding servers may or may not participate in this computation. Note that each secret component is a function of both the user's weak secret data and of the strong secret data for the corresponding secret holding server.

For example, if the generating client 120 has direct knowledge of the server secret data b(i), then it can directly compute 534 the secret components $K(i)=h(w^{b(i)})$. Alternately, if the generating client 120 does not have access to the server secret data b(i), then the following protected transaction method may be used. The generating client 120 selects a client ephemeral secret which is a random integer a for which there exists a corresponding integer a' such that $x^{aa'}=x$ for all x in group G. For example, if G is the group of integers modulo p, a may be selected to be an element of the multiplicative group of integers modulo p−1 and a' would then be its multiplicative inverse. The generating client computes and sends a message $M1=w^a$ to each secret holding server S(i). Secret holding server S(i) computes $c(i)=M1^{b(i)}=w^{a\ b(i)}$ and sends c(i) to the generating client 120. The generating client 120 computes the value a' corresponding to a and then computes 534 the secret component $K(i)=h(c(i)^{a'})=h(w^{b(i)})$. This approach ensures that no secret data is exposed to an eavesdropper, by making use of the encrypting properties of discrete exponentiation.

Once the generating client 120 has computed 534 the secret components K(i), it then computes 536 the strong secret K as a function of the secret-components K(i) of the participating secret holding servers S(i). In this example, the strong secret K is calculated 536 according to a bit-wise exclusive-OR, $K=K(1)\oplus K(2)\oplus \ldots \oplus K(N)$ where $\oplus$ denotes exclusive-OR. Binary addition and t-out-of-N threshold secret sharing methods are two other methods for combining the secret components K(i). In a t-out-of N threshold secret sharing method, there are N secret holding servers but the strong secret data can be computed from recovery data from only t of them, where t is less than N. Other methods will be apparent.

In the storage stage 503, the strong secret data K is used as a cryptographic key in a symmetric cryptosystem to encrypt 370 a user's private data including a private key $Priv_u$. The encrypted private data, denoted by EPD, which includes the encrypted private key, denoted by $E_K(Priv_u)$, where $E_K$ means encrypted with key K, is stored 375 in storage medium 140.

In the verifier setup stage 502, the public key, $Pub_u$, corresponding to the user's private key, $Priv_u$, might be used as the verifier data v(i). In this embodiment, each secret holding server also plays the role of a verification server S(i) and stores 355 its verifier data $v(i)=Pub_u$ or at least has access to the public key. In an alternate approach, the verifier data v(i)=h(K, Id(i)), where Id(i) is a unique but publicly known identifier for server S(i) and h is a one-way function such as a hash function. The inclusion of Id(i) ensures that different verifier data is produced for each verification server.

Referring now to FIG. 6, the recovery process 600 also includes three stages 601–603. In stage 601, the recovery client 220 recovers the user's strong secret K based on his weak secret PWD, with the assistance of the secret holding servers. In the verification stage 602, the recovery client 220 proves to the verification servers that it has successfully recovered the strong secret K. In stage 603, the recovery client 220 recovers the user's private key, $Priv_u$.

Recovery 601 of the strong secret K begins with the recovery client 220 receiving 410 the user account identifier U and password PWD from the user 110. The recovery client 220 then regenerates the required secret components K(i) using the protected transaction method described above. In particular, the recovery client 220 computes 622 w=f(PWD), where f is the same one-way function used in the generation stage 500. The recovery client 220 selects 624 an ephemeral client secret which is a random integer a for which there exists a corresponding integer a' such that $x^{aa'}=x$ for all x in group G. For example, if G is the group of integers modulo p, a may be selected to be an element of the multiplicative group of integers modulo p−1 and a' would then be its multiplicative inverse. The recovery client then computes 626 the server request data $M^1=W^a$ and transmits 625 this server request data to server S(i). Note that the server request data $M^1$ is a function of both the weak secret data PWD and of the ephemeral client secret a. However, the server request data $M_1$ does not reveal information about the weak secret data PWD without knowledge of the ephemeral client secret a.

Server S(i) receives the server request data $M_1$. The server increments a counter of unverified recovery attempts for user account U and the current password PWD and determines 680 whether it is likely that a party without access to the password is attempting to regenerate the strong secret data. In this embodiment, it does so by determining whether the number of unverified recovery attempts exceeds a threshold. If it does, then the server disables the user account U and aborts the recovery process 600. Depending on the properties of the group G, the server may also verify that server request data $M_1$ satisfies necessary strength properties. If the server request data $M_1$ does not have the requisite strength properties, then the server aborts the recovery process. If the recovery process has not been aborted, the server computes 630 the server response data $c(i)=M_1^{b(i)}=w^{ab(i)}$ and sends 635 c(i) to the recovery client 220. The server also generates 690 a unique index n(i), or nonce, for this instantiation of the recovery process and transmits the nonce to the recovery client 220. The server sets a state variable indicating verification pending for nonce n(i). In a preferred approach, the server transmits to the recovery client 220 a single message, which is based on both the server response data c(i) and the nonce n(i). Similar to the server request data $M_1$, the server response data c(i) is a function of the server secret data b(i) for the secret holding server and of the server request data $M_1$ received. However, the server response data c(i) does not reveal information about the server secret data b(i) without knowledge of the server request data $M_1$, or somewhat equivalently, of the weak secret data PWD and ephemeral client secret a.

Upon receipt of the message from the server, the recovery client 220 may abort the recovery process 600 if the received message does not have the requisite strength. Otherwise, the recovery client 220 computes 642 the value a' that corresponds to a. It then computes 644 the secret component $K(i)=h(c(i)^{a'})=h(w^{b(i)})$. Note that use of the ephemeral client secret a makes the communications between recovery client 220 and secret holding server 130 resistant to attacks intended to deduce the weak secret data PWD or server secret data b(i). However, the secret component K(i) is a function of both the weak secret data PWD and server secret data b(i), but is independent of the ephemeral client secret a. Finally, the recovery client 220 computes 646 the strong secret data $K=K(1)\oplus K(2) \oplus \ldots \oplus K(N)$. The recovery client 220 can then recover the user's private key $Priv_u$ by retrieving 475 and decrypting 470 EPD using the recovered cryptographic key K.

As mentioned previously, different verification approaches may be used. For example, assume that the user's public key $Pub_u$ is used as the verifier data v(i). Then, the recovery client 220 can generate 650 proof data by digitally signing a message containing the various nonces n(i) using the user's recovered private key $Priv_u$. Each verification server verifies 660 successful recovery of the strong secret data K by verifying the digital signature using the user's public key $Pub_u$, and then verifying that the correct nonce n(i) is included in the message. On the other hand, assume that the verifier data v(i)=h(K, Id(i)). Then, the proof data can be computed according to the expression g(v(i), n(i)) where g is a one-way function such as a cryptographic hash function. The verification server verifies 660 the proof data by computing its own value from its own knowledge of v(i) and n(i), and comparing the result with the value received.

Upon receipt of the proof data, each server determines whether the state variable indicates verification pending for nonce n(i). If verification is pending, then the server verifies that the received proof data successfully demonstrates knowledge of strong secret K and freshness linked to nonce n(i). If both of these are verified, then the counter of unverified recovery attempts for user account U and password PWD are decremented. Otherwise, the recovery process is considered to be unsuccessful.

Methods 300, 400, 500 and 600 are particularly advantageous because they are resistant to many types of attacks, including attacks by or on the servers S(i). The following are some types of attacks and examples countermeasures.

An attacker may attempt to guess or otherwise compromise the user 110's password PWD. This may be combated by placing requirements on the choice of password PWD in order to reduce the chance that an attacker will guess the password. For example, the password may be required to have a minimum length or to be changed periodically. In another countermeasure, an attempt-threshold which limits the number of guesses at the password PWD is selected. Thus, an attacker has only a limited number of tries to guess the password PWD. If the attempt-threshold is exceeded, the generation process 500 preferably is re-executed, requiring a new password PWD and generating a new strong secret K, thus foiling the attacker. The attempt-threshold preferably should be set so that, given the requirements placed on the password, the probability of a successful guessing attack is acceptably small while still balancing the reality that some unsuccessful attempts may be legitimate rather than the byproduct of an attack. For example, an unsuccessful attempt may be legitimately recorded in the absence of any attack, if the user 110 incorrectly types his password PWD and/or as a result of a communications or system failure.

Alternately, an attacker might try to compromise the protocol by computing w, a, and/or b(i) from the messages transmitted among the various components. However, this attack may be defeated by selecting group G so as to be resistant to discrete-logarithm attacks. For example, when G is the set of integers modulo a prime p then p is selected so as to be a sufficiently strong Diffie-Hellman modulus (e.g., a safe prime) according to well-known rules. Then, such attacks will be infeasible due to the discrete logarithm problem. This is also true for an attacking server. It is infeasible for a server to compute w, a, and/or any b(i) other than its own. The selection of a strong prime p also results in a strong secret K, thus making it infeasible to directly attack ciphertext encrypted under the strong secret K.

In another type of attack, the attacker might pose as a recovery client and send weak server request data $M_1$ to the server S(i), with the intention of obtaining some information about the server secret data b(i) when the server returns the server response data $c(i)=M_1^{b(i)}$. The main known attack of this type relates to the small-subgroup attack on Diffie-Hellman cryptosystems. This can be averted by various means, including initial selection of prime p with suitable properties, such as a safe prime of the form p=2q+1 where q is a prime, and by making b(i) always an even number. Depending on the properties of the particular type of group G, the server S(i) can also check the strength of the received $M_1$ and refuse to respond if it recognizes it as a weak value.

An attacker might attempt to close down or force a password change on a user account or multiple accounts supported by a server S(i) by either sending repeated false server request data $M_1$ or by disrupting protocols by, for example, intercepting and discarding messages conveying server response data or proof data. The goal of this attack is to cause the server to disable one or more user accounts. The impact of this attack can be reduced by having servers S(i) "throttle" the processing of repeated $M_1$ requests for a user account. That is, the server S(i) suspends or delays processing for a user account in the face of multiple unsuccessful attempts during some time period.

Alternately, an attacker might attempt to overload a server S(i) by sending massive numbers of false $M_1$ to the server, thus causing it to perform massive numbers of useless but computationally intensive exponentiations. To the extent such attempts are for the same user account, throttling (as discussed above) will significantly combat this attack. Thus, the attack is viable primarily if large numbers of different user accounts are used. Hence, it can be resisted by making it difficult to guess a valid user account identifier U, for example by avoiding user account identifiers drawn from a simple number sequence.

As a final example, a communications or system failure at one server might cause multiple recovery protocol failures at the other servers, resulting in the unnecessary disabling and forced password-change of one or more user accounts. To reduce this problem, servers preferably should be designed for high availability, with appropriate redundancy of systems and communications paths. In addition, if one server unavoidably fails, management controls may temporarily suspend operation of the other servers. Throttling (as discussed above) will also reduce the incidence of account disabling.

The above description is included to illustrate the operation of the preferred embodiments and is not meant to limit the scope of the invention. From the above discussion, many variations will be apparent to one skilled in the art that would be encompassed by the spirit and scope of the present invention. For example, the presence of a hardware token may be required in order to complete recovery process 400. In one approach, recovery client 220 determines whether the user's hardware token is present and, if it is, the recovery client 220 then transmits data attesting to or proving this fact to each secret holding server. The servers, in turn, participate in the regeneration process only if they receive this data from the recovery client 220. When used in conjunction with a hardware token, such as a challenge-response token or time-synchronized one-time password generator, in such a way that the recovery client 220 additionally proves possession of the token to one or more servers, the resulting combination of methods can effectively serve in place of a smartcard method in which a strong secret is recovered from the smartcard in response to presentation of a user weak secret such as a PIN. The advantage of the former approach over the smartcard approach is a possible major reduction in deployment and maintenance cost since the aforementioned types of tokens do not require special hardware interfaces, as are required by smartcards. Hence, the scope of the invention is to be limited only by the following claims.

What is claimed is:

1. A method for enabling devices to securely regenerate a user's strong secret data from weak secret data for the user, the method comprising:
   determining the user's weak secret data;
   computing secret components for each of at least two secret holding servers, wherein the secret component for each secret holding server is a function of the user's weak secret data and of server secret data for the secret holding server, said computing secret components includes, for at least one secret holding server:
      computing server request data for the secret holding server, wherein the server request data is a function of the weak secret data and of an ephemeral client secret, and the server request data does not reveal information about the weak secret data without knowledge of the ephemeral client secret,
      receiving server response data from the secret holding server, wherein the server response data is a function of the server secret data for the secret holding server and of the server request data, and the server response data does not reveal information about the server secret data without knowledge of the weak secret data and the ephemeral client secret, and
      computing the secret component for the secret holding server as a function of the server response data received from the secret holding server and of the ephemeral client secret, wherein the secret component is a function of the weak secret data and of the server secret data but is independent of the ephemeral client secret;
   computing the user's strong secret data, wherein the strong secret data is a function of the secret components for the secret holding servers; and
   determining verifier data for each of at least two verification servers, wherein the verifier data for each verification server enables the verification server to verify that a device has successfully recovered the strong secret data but it is computationally infeasible for the verification server to determine the weak secret data based only on access to its verifier data.

2. The method of claim 1 wherein:
   the server secret data for at least one secret holding server i includes a random integer b(i), where i is an index for the secret holding servers;
   the step of computing the server request data for the secret holding server i comprises computing the value $M=w^a$ wherein
      w=f(weak secret data), wherein f is a function which generates an element of a finite group G in which exponentiation is efficient but the discrete logarithm problem is computationally infeasible; and
      the ephemeral client secret includes the random integer a for which there exists a corresponding integer a' such that $x^{aa'}=x$ for all x in the group G;
   the step of receiving the server response data comprises receiving the value $c(i)=M^{b(i)}$ wherein the exponentiation is computed in the group G; and
   the step of computing the secret component comprises computing the value $K(i)=h(c(i)^{a'})$ wherein h is a function and the exponentiation is computed in the group G.

3. The method of claim 2 wherein the group G is selected from:
   a multiplicative group of the set of integers modulo p, where p is a large prime suitable as a Diffie-Hellman modulus; and
   a group of points on an elliptic curve over a finite field.

4. A method for enabling devices to securely regenerate a user's strong secret data from weak secret data for the user, the method comprising:
   determining the user's weak secret data;
   computing secret components for each of at least two secret holding servers, wherein the secret component for each secret holding server is a function of the user's weak secret data and of server secret data for the secret holding server;

computing the user's strong secret data, wherein the strong secret data is a function of the secret components for the secret holding servers;

encrypting private data for the user using the strong secret data as a cryptographic key in a symmetric cryptosystem; and determining verifier data for each of at least two verification servers, wherein the verifier data for each verification server enables the verification server to verify that a device has successfully recovered the strong secret data but it is computationally infeasible for the verification server to determine the weak secret data based only on access to its verifier data, said determining verifier data includes, for at least one verification server, determining public data which corresponds to the user's private data, wherein a first entity with access to the private data can prove said access to a second entity with access to the public data without disclosing the private data to the second entity.

5. A method for securely regenerating a user's strong secret data from weak secret data for the user, the method comprising:

receiving the user's weak secret data;

computing secret components for each of at least two secret holding servers, wherein the secret component for each secret holding server is a function of the user's weak secret data and of server secret data for the secret holding server, said computing secret components includes, for at least one secret holding server;

computing server request data for the secret holding server, wherein the server request data is a function of the weak secret data and of an ephemeral client secret, and the server request data does not reveal information about the weak secret data without knowledge of the ephemeral client secret, receiving server response data from the secret holding server, wherein the server response data is a function of the server secret data for the secret holding server and of the server request data, and the server response data does not reveal information about the server secret data without knowledge of the weak secret data and the ephemeral client secret, and computing the secret component for the secret holding server as a function of the server response data received from the secret holding server and of the ephemeral client secret, wherein the secret component is a function of the weak secret data and of the server secret data but is independent of the ephemeral client secret;

computing the user's strong secret data, wherein the strong secret data is a function of the secret components for the secret holding servers;

determining proof data for proving to at least two verification servers that the strong secret data was successfully computed; and transmitting the proof data to the verification servers.

6. The method of claim 5 wherein:

the server secret data for at least one secret holding server i includes a random integer $b(i)$, where i is an index for the secret holding servers;

the step of computing the server request data for the secret holding server i comprises computing the value $M=w^a$ wherein $w=f(\text{weak secret data})$, wherein f is a function which generates an element of a finite group G in which exponentiation is efficient but the discrete logarithm problem is computationally infeasible; and the ephemeral client secret includes the random integer a for which there exists a corresponding integer a' such that $x^{aa'}=x$ for all x in the group G;

the step of receiving the server response data comprises receiving the value $c(i)=M^{b(i)}$ wherein the exponentiation is computed in the group G; and the step of computing the secret component comprises computing the value $K(i)=h(c(i)^{a'})$ wherein h is a function and the exponentiation is computed in the group G.

7. The method of claim 6 wherein the group G is selected from:

a multiplicative group of the set of integers modulo p, where p is a large prime suitable as a Diffie-Hellman modulus; and a group of points on an elliptic curve over a finite field.

8. A method for securely regenerating a user's strong secret data from weak secret data for the user, the method comprising:

receiving the user's weak secret data;

computing secret components for each of at least two secret holding servers, wherein the secret component for each secret holding server is a function of the user's weak secret data and of server secret data for the secret holding server, said computing secret components;

computing the user's strong secret data, wherein the strong secret data is a function of the secret components for the secret holding servers;

obtaining encrypted private data for the user, wherein a first entity with access to the private data can prove said access to a second entity with access to corresponding public data without disclosing the private data to the second entity, and decrypting the encrypted private data using the strong secret data as a cryptographic key in a symmetric cryptosystem;

determining proof data for proving to at least two verification servers that the strong secret data was successfully computed, said determining proof data includes, for at least one verification server, determining proof data based on the decrypted private data; and transmitting the proof data to the verification servers.

9. The method of claim 8 wherein the step of determining proof data comprises:

determining proof data as a function of a nonce which distinguishes the proof data from other instances of proof data provided for the user.

10. The method of claim 9 wherein:

the user's private data includes a private key for use in a digital signature system; and the step of determining proof data comprises digitally signing a message containing the nonce using the private key.

11. A method for securely regenerating a user's strong secret data from weak secret data for the user, the method comprising:

receiving the user's weak secret data;

computing secret components for each of at least two secret holding servers, wherein the secret component for each secret holding server is a function of the user's weak secret data and of server secret data for the secret holding server;

computing the user's strong secret data, wherein the strong secret data is a function of the secret components for the secret holding servers;

determining proof data for proving to at least two verification servers that the strong secret data was successfully computed, said determining proof data includes:
computing the proof data as a one-way function of the strong secret data, and
determining the proof data as a function of a nonce which distinguishes the proof data from other instances of proof data provided for the user; and
transmitting the proof data to the verification servers.

12. The method of claim 11 wherein the step of determining proof data comprises:
computing verifier data for the verification server as a one-way function of the strong secret data; and
computing the proof data as a one-way function of the verifier data and the nonce.

13. A method for securely regenerating a user's strong secret data from weak secret data for the user, the method comprising:
receiving the user's weak secret data;
computing secret components for each of at least two secret holding servers, wherein the secret component for each secret holding server is a function of the user's weak secret data and of server secret data for the secret holding server;
computing the user's strong secret data, wherein the strong secret data is a function of the secret components for the secret holding servers;
determining proof data for proving to at least two verification servers that the strong secret data was successfully computed;
transmitting the proof data to the verification servers;
determining token possession proof data for proving presence of a user's hardware token; and
transmitting the token possession proof data to at least one server selected from a group of consisting of the secret holding servers and the verification servers.

14. A method for securely regenerating a user's strong secret data from weak secret data for the user, the method comprising:
receiving the user's weak secret data;
computing secret components for each of at least two secret holding servers, wherein the secret component for each secret holding server is a function of the user's weak secret data and of server secret data for the secret holding server;
computing the user's strong secret data, wherein the strong secret data is a function of the secret components for the secret holding servers;
determining proof data for proving to at least two verification servers that the strong secret data was successfully computed, said determining proof data includes determining the proof data as a function of user data which the verification server can authenticate as originating from the user; and
transmitting the proof data to the verification servers.

15. The method of claim 14 further comprising:
receiving digital signature components from at least two verification servers, wherein the user data comprises a user-originated message, and
computing a digital signature of the user-originated message as a function of digital signature components.

16. A method for facilitating secure regeneration of a user's strong secret data from weak secret data for the user, the method comprising:
receiving server request data from a device attempting to recover a user's strong secret data, wherein:
the strong secret data is a function of the user's weak secret data and of the server secret data for at least one secret holding server, and
the server request data is a function of the weak secret data and of an ephemeral client secret, and the server request data does not reveal information about the weak secret data without knowledge of the ephemeral client secret;
computing server response data as a function of server secret data for the user and the server request data, and the server response data does not reveal information about the server secret data without knowledge of the weak secret data and the ephemeral client secret; and
transmitting the server response data to the device responsive to a determination that it is unlikely that a party without access to the weak secret data is attempting to regenerate the strong secret data.

17. The method of claim 16 wherein:
the server secret data includes a random integer b;
the server request data includes a value $M=w^a$, where $w=f(\text{user secret data})$, wherein f is a function which generates an element of a finite group G in which exponentiation is efficient but the discrete logarithm problem is computationally infeasible;
a is an ephemeral client secret; and
the exponentiation $w^a$ is computed in the group G; and
the step of computing the server response data includes computing a value $M^b$ wherein the exponentiation is computed in the group G.

18. The method of claim 17 wherein the group G is selected from:
a multiplicative group of the set of integers modulo p, where p is a large prime suitable as a Diffie-Hellman modulus; and
a group of points on an elliptic curve over a finite field.

19. The method of claim 16 wherein the server response data includes a nonce which distinguishes the server response data from other instances of server response data provided by the secret holding server for the user.

20. The method of claim 16 further comprising:
accessing verifier data, wherein the verifier data enables a verification server to verify that a device has successfully recovered the strong secret data;
receiving proof data from the device;
responsive to the verifier data and the proof data received from the device, determining whether the device has successfully regenerated the strong secret data; and
responsive to a determination that the device has not successfully recovered the strong secret data, updating a record of unsuccessful attempts to recover the strong secret data.

21. The method of claim 20 wherein:
the verifier data includes public data which corresponds to a user's private data, wherein a first entity with access to the private data can prove said access to a second entity with access to the public data without disclosing the private data to the second entity; and
the step of determining whether the device has successfully recovered the strong secret data comprises determining whether the proof data proves that the device has access to the private data.

22. The method of claim 21 wherein:

the step of determining whether the device has successfully recovered the strong secret data further comprises determining whether the proof data proves that the device has access to a nonce which confirms freshness of the proof data.

23. The method of claim 22 wherein:

the user's private data includes a private key for use in a digital signature system;

the proof data includes digitally signed data which allegedly contains the nonce and allegedly has been digitally signed using the private key;

the step of determining whether the proof data proves that the device has access to the private data includes verifying that the digitally signed data has been digitally signed using the private key; and the step of determining whether the proof data proves that the device has access to the nonce includes verifying that the digitally signed data contains the nonce or a value derived from the nonce.

24. The method of claim 20 wherein:

the verifier data is a one-way function of the strong secret data; and the step of determining whether the device has successfully recovered the strong secret data comprises determining whether the proof data proves that the device can compute the verifier data.

25. The method of claim 24 wherein:

the step of determining whether the device has successfully recovered the strong secret data further comprises determining whether the proof data proves that the device has access to a nonce which confirms freshness of the proof data.

26. The method of claim 25 wherein the step of determining whether the device has successfully recovered the strong secret data comprises:

computing an expected proof data as a one-way function of the verifier data and the nonce; and comparing the expected proof data with the proof data received from the device.

27. The method of claim 16 further comprising:

accessing verifier data, wherein the verifier data enables a verification server to verify that a device has successfully recovered the strong secret data;

receiving proof data from the device, the proof data including a user-originated message to be digitally signed;

responsive to the verifier data and the proof data received from the device, determining whether the device has successfully regenerated the strong secret data; and responsive to a determination that the device has successfully recovered the strong secret data, generating a digital signature component based on the user-originated message, wherein a digital signature of the user-originated message is a function of the digital signature components for at least two verification servers; and transmitting the digital signature component to the device.

28. The method of claim 16 further comprising:

receiving token possession proof data for proving presence of a user's hardware token;

wherein the step of transmitting server response data to the device is responsive to a determination that the user's hardware token is present.

29. A method for enabling devices to securely regenerate a user's strong secret data from weak secret data for the user, the method comprising:

determining the user's weak secret data;

computing server request data for a secret holding server, wherein the server request data is a function of the weak secret data and of an ephemeral client secret, and the server request data does not reveal information about the weak secret data without knowledge of the ephemeral client secret;

receiving server response data from the secret holding server, wherein the server response data is a function of the server secret data for the secret holding server and of the server request data, and the server response data does not reveal information about the server secret data without knowledge of the weak secret data and the ephemeral client secret;

computing a secret component for the secret holding server as a function of the server response data received from the secret holding server and of the ephemeral client secret, wherein the secret component is a function of the weak secret data and of the server secret data but is independent of the ephemeral client secret;

computing the user's strong secret data as a function of the secret component; and determining verifier data for at least one verification server, wherein the verifier data enables the verification server to verify that a device has successfully recovered the strong secret data but it is computationally infeasible for the verification server to determine the weak secret data based only on access to its verifier data.

30. The method of claim 29 wherein:

the server secret data includes a random integer b;

the secret component is a value $K=h(w^b)$, wherein h is a function;

w=f(weak secret data), wherein f is a function which generates an element of a finite group G in which exponentiation is efficient but the discrete logarithm problem is computationally infeasible; and the exponentiation $w^b$ is computed in the group G;

the ephemeral client secret is a random integer a for which there exists a corresponding integer a' such that $x^{aa'}=x$ for all x in group G;

the server request data is computed as the value $M=w^a$ wherein the exponentiation is computed in the group G;

the server response data is computed as the value $c=M^b$ wherein the exponentiation is computed in the group G; and the secret component is computed as the value $K=h(c^{a'})$ wherein the exponentiation is computed in the group G.

31. The method of claim 30 wherein the group G is selected from:

a multiplicative group of the set of integers modulo p, where p is a large prime suitable as a Diffie-Hellman modulus; and a group of points on an elliptic curve over a finite field.

32. The method of claim 29 further comprising:

encrypting private data for the user using the strong secret data as a cryptographic key in a symmetric cryptosystem; wherein the step of determining verifier data includes determining public data which corresponds to the user's private data, wherein a first entity with access to the private data can prove said access to a second entity with access to the public data without disclosing the private data to the second entity.

33. The method of claim 29 wherein the step of determining verifier data comprises computing verifier data as a one-way function of the strong secret data.

34. A method for securely regenerating a user's strong secret data from weak secret data for the user, the method comprising:

receiving the user's weak secret data;

computing server request data for a secret holding server, wherein the server request data is a function of the weak secret data and of an ephemeral client secret, and the server request data does not reveal information about the weak secret data without knowledge of the ephemeral client secret;

receiving server response data from the secret holding server, wherein the server response data is a function of the server secret data for the secret holding server and of the server request data, and the server response data does not reveal information about the server secret data without knowledge of the weak secret data and the ephemeral client secret;

computing a secret component for the secret holding server as a function of the server response data received from the secret holding server and of the ephemeral client secret, wherein the secret component is a function of the weak secret data and of the server secret data but is independent of the ephemeral client secret;

computing the user's strong secret data as a function of the secret component;

determining proof data for proving to at least one verification server that the strong secret data was successfully computed; and transmitting the proof data to the verification servers.

35. The method of claim 34 wherein:

the server secret data includes a random integer b; and the secret component is a value $K=h(w^b)$, wherein h is a function;

w=f(weak secret data), wherein f is a function which generates an element of a finite group G in which exponentiation is efficient but the discrete logarithm problem is computationally infeasible; and the exponentiation $w^b$ is computed in the group G;

the ephemeral client secret is a random integer a for which there exists a corresponding integer a' such that $x^{aa'}=x$ for all x in group G;

the server request data is computed as the value $M=w^a$ wherein the exponentiation is computed in the group G;

the server response data is computed as the value $c=M^b$ wherein the exponentiation is computed in the group G; and the secret component is computed as the value $K=h(c^{a'})$ wherein the exponentiation is computed in the group G.

36. The method of claim 35 wherein the group G is selected from:

a multiplicative group of the set of integers modulo p, where p is a large prime suitable as a Diffie-Hellman modulus; and a group of points on an elliptic curve over a finite field.

37. The method of claim 34 further comprising:

obtaining encrypted private data for the user, wherein a first entity with access to the private data can prove said access to a second entity with access to corresponding public data without disclosing the private data to the second entity; and decrypting the encrypted private data using the strong secret data as a cryptographic key in a symmetric cryptosystem; wherein the step of determining proof data comprises computing proof data based on the decrypted private data.

38. The method of claim 37 wherein the step of determining proof data comprises determining proof data as a function of a nonce which distinguishes the proof data from other instances of proof data provided for the user.

39. The method of claim 38 wherein:

the user's private data includes a private key for use in a digital signature system; and the step of determining proof data comprises digitally signing a message containing the nonce using the private key.

40. The method of claim 34 wherein the step of determining proof data comprises computing proof data as a one-way function of the strong secret data.

41. The method of claim 40 wherein:

the step of determining proof data comprises determining the proof data as a function of a nonce which distinguishes the proof data from other instances of proof data provided for the user.

42. The method of claim 41 wherein the step of determining proof data comprises:

computing verifier data as a one-way function of the strong secret data; and computing the proof data as a one-way function of the verifier data and of the nonce.

43. The method of claim 34 further comprising:

determining token possession proof data for proving presence of a user's hardware token; and transmitting the token possession proof data to at least one server selected from a group consisting of the secret holding servers and the verification servers.

44. A computer program product having instructions executable by a generating client for instructing the generating client to perform method steps for enabling devices to securely regenerate a user's strong secret data from weak secret data for the user, the method steps comprising:

determining the user's weak secret data;

computing secret components for each of at least two secret holding servers, wherein the secret component for each secret holding server is a function of the user's weak secret data and of the server secret data for the secret holding server, said computing secret components includes, for at least one secret holding server:

computing server request data for the secret holding server, wherein the server request data is a function of the weak secret data and of an ephemeral client secret, and the server request data does not reveal information about the weak secret data without knowledge of the ephemeral client secret, receiving server response data from the secret holding server, wherein the server response data is a function of the server secret data for the secret holding server and of the server request data, and the server response data does not reveal information about the server secret data without knowledge of the weak secret data and the ephemeral client secret, and computing the secret component for the secret holding server as a function of the server response data received from the secret holding server and of the ephemeral client secret, wherein the secret component is a function of the weak secret data and of the server secret data but is independent of the ephemeral client secret;

computing the user's strong secret data, wherein the strong secret data is a function of the secret components for the secret holding servers; and determining verifier data for each of at least two verification servers, wherein the verifier data for each verification server enables the verification server to verify that a device has successfully recovered the strong secret data but it is computationally infeasible for the verification server to determine the weak secret data based only on access to its verifier data.

45. The computer program product of claim 44 wherein:

the server secret data for at least one secret holding server i includes a random integer b(i), where i is an index for the secret holding servers;

the step of computing the server request data for the secret holding server i comprises computing the value $M=w^a$ wherein w=f(weak secret data), wherein f is a function which generates an element of a finite group G in which exponentiation is efficient but the discrete logarithm problem is computationally infeasible; and the ephemeral client secret includes the random integer a for which there exists a corresponding integer a' such that $x^{aa'}=x$ for all x in the group G;

the step of receiving the server response data comprises receiving the value $c(i)=M^{b(i)}$ wherein the exponentiation is computed in the group G; and the step of computing the secret component comprises computing the value $K(i)=h(c(i)^{a'})$ wherein h is a function and the exponentiation is computed in the group G.

46. The computer program product of claim 45 wherein the group G is selected from:

a multiplicative group of the set of integers modulo p, where p is a large prime suitable as a Diffie-Hellman modulus; and a group of points on an elliptic curve over a finite field.

47. A computer program product having instructions executable by a generating client for instructing the generating client to perform method steps for enabling devices to securely regenerate a user's strong secret data from weak secret data for the user, the method steps comprising:

determining the user's weak secret data;

computing secret components for each of at least two secret holding servers, wherein the secret component for each secret holding server is a function of the user's weak secret data and of server secret data for the secret holding server;

computing the user's strong secret data, wherein the strong secret data is a function of the secret components for the secret holding servers;

encrypting private data for the user using the strong secret data as a cryptographic key in a symmetric cryptosystem; and determining verifier data for each of at least two verification servers, wherein the verifier data for each verification server enables the verification server to verify that a device has successfully recovered the strong secret data but it is computationally infeasible for the verification server to determine the weak secret data based only on access to its verifier data, said determining verifier data includes, for at least one verification server, determining public data which corresponds to the user's private data, wherein a first entity with access to the private data can prove said access to a second entity with access to the public data without disclosing the private data to the second entity.

48. A computer program product having instructions executable by a generating client for instructing the generating client to perform method steps for enabling devices to securely regenerate a user's strong secret data from weak secret data for the user, the method steps comprising:

receiving the user's weak secret data;

computing secret components for each of at least two secret holding servers, wherein the secret component for each secret holding server is a function of the user's weak secret data and of server secret data for the secret holding server, said computing secret components includes, for at least one secret holding server;

computing server request data for the secret holding server, wherein the server request data is a function of the weak secret data and of an ephemeral client secret, and the server request data does not reveal information about the weak secret data without knowledge of the ephemeral client secret, receiving server response data from the secret holding server, wherein the server response data is a function of the server secret data for the secret holding server and of the server request data, and the server response data does not reveal information about the server secret data without knowledge of the weak secret data and the ephemeral client secret, and computing the secret component for the secret holding server as a function of the server response data received from the secret holding server and of the ephemeral client secret, wherein the secret component is a function of the weak secret data and of the server secret data but is independent of the ephemeral client secret;

computing the user's strong secret data, wherein the strong secret data is a function of the secret components for the secret holding servers;

determining proof data for proving to at least two verification servers that the strong secret data was successfully computed; and transmitting the proof data to the verification servers.

49. The computer program product of claim 48 wherein:

the server secret data for at least one secret holding server i includes a random integer b(i), where i is an index for the secret holding servers;

the step of computing the server request data for the secret holding server i comprises computing the value $M=w^a$ wherein w=f(weak secret data), wherein f is a function which generates an element of a finite group G in which exponentiation is efficient but the discrete logarithm problem is computationally infeasible; and the ephemeral client secret includes the random integer a for which there exists a corresponding integer a' such that $x^{aa'}=x$ for all x in the group G;

the step of receiving the server response data comprises receiving the value $c(i)=M^{b(i)}$ wherein the exponentiation is computed in the group G; and the step of computing the secret component comprises computing the value $K(i)=h(c(i)^{a'})$ wherein h is a function and the exponentiation is computed in the group G.

50. The computer program product of claim 49 wherein the group G is selected from:

a multiplicative group of the set of integers modulo p, where p is a large prime suitable as a Diffie-Hellman modulus; and a group of points on an elliptic curve over a finite field.

51. A computer program product having instructions executable by a generating client for instructing the generating client to perform method steps for enabling devices to securely regenerate a user's strong secret data from weak secret data for the user, the method steps comprising:

receiving the user's weak secret data;

computing secret components for each of at least two secret holding servers, wherein the secret component for each secret holding server is a function of the user's weak secret data and of server secret data for the secret holding server, said computing secret components;

computing the user's strong secret data, wherein the strong secret data is a function of the secret components for the secret holding servers;

obtaining encrypted private data for the user, wherein a first entity with access to the private data can prove said access to a second entity with access to corresponding public data without disclosing the private data to the second entity, and decrypting the encrypted private data using the strong secret data as a cryptographic key in a symmetric cryptosystem;

determining proof data for proving to at least two verification servers that the strong secret data was successfully computed, said determining proof data includes, for at least one verification server, determining proof data based on the decrypted private data; and transmitting the proof data to the verification servers.

52. The computer program product of claim 51 wherein the step of determining proof data comprises:

determining proof data as a function of a nonce which distinguishes the proof data from other instances of proof data provided for the user.

53. The computer program product of claim 52 wherein:

the user's private data includes a private key for use in a digital signature system; and the step of determining proof data comprises digitally signing a message containing the nonce using the private key.

54. A computer program product having instructions executable by a generating client for instructing the generating client to perform method steps for enabling devices to securely regenerate a user's strong secret data from weak secret data for the user, the method steps comprising:

receiving the user's weak secret data;

computing secret components for each of at least two secret holding servers, wherein the secret component for each secret holding server is a function of the user's weak secret data and of server secret data for the secret holding server;

computing the user's strong secret data, wherein the strong secret data is a function of the secret components for the secret holding servers;

determining proof data for proving to at least two verification servers that the strong secret data was successfully computed, said determining proof data includes:

computing the proof data as a one-way function of the strong secret data, and determining the proof data as a function of a nonce which distinguishes the proof data from other instances of proof data provided for the user; and transmitting the proof data to the verification servers.

55. The computer program product of claim 54 wherein the step of determining proof data comprises:

computing verifier data for the verification server as a one-way function of the strong secret data; and computing the proof data as a one-way function of the verifier data and the nonce.

56. A computer program product having instructions executable by a generating client for instructing the generating client to perform method steps for enabling devices to securely regenerate a user's strong secret data from weak secret data for the user, the method steps comprising:

receiving the user's weak secret data;

computing secret components for each of at least two secret holding servers, wherein the secret component for each secret holding server is a function of the user's weak secret data and of server secret data for the secret holding server;

computing the user's strong secret data, wherein the strong secret data is a function of the secret components for the secret holding servers;

determining proof data for proving to at least two verification servers that the strong secret data was successfully computed;

transmitting the proof data to the verification servers;

determining token possession proof data for proving presence of a user's hardware token; and transmitting the token possession proof data to at least one server selected from a group of consisting of the secret holding servers and the verification servers.

57. A computer program product having instructions executable by a generating client for instructing the generating client to perform method steps for enabling devices to securely regenerate a user's strong secret data from weak secret data for the user, the method steps comprising:

receiving the user's weak secret data;

computing secret components for each of at least two secret holding servers, wherein the secret component for each secret holding server is a function of the user's weak secret data and of server secret data for the secret holding server;

computing the user's strong secret data, wherein the strong secret data is a function of the secret components for the secret holding servers;

determining proof data for proving to at least two verification servers that the strong secret data was successfully computed, said determining proof data includes determining the proof data as a function of user data which the verification server can authenticate as originating from the user; and transmitting the proof data to the verification servers.

58. The computer program product of claim 57 wherein the method steps further comprise:

receiving digital signature components from at least two verification servers, wherein the user data comprises a user-originated message, and computing a digital signature of the user-originated message as a function of digital signature components.

59. A computer program product having instructions executable by a server for instructing the server to perform method steps for facilitating secure regeneration of a user's strong secret data from weak secret data for the user, the method steps comprising:

receiving server request data from a device attempting to recover a user's strong secret data, wherein:

the strong secret data is a function of the user's weak secret data and of the server secret data for at least one secret holding server, and the server request data is a function of the weak secret data and of an ephemeral client secret, and the server request data does not reveal information about the weak secret data without knowledge of the ephemeral client secret;

computing server response data as a function of server secret data for the user and the server request data, and the server response data does not reveal information about the server secret data without knowledge of the weak secret data and the ephemeral client secret; and transmitting the server response data to the device responsive to a determination that it is unlikely that a party without access to the weak secret data is attempting to regenerate the strong secret data.

60. The computer program product of claim 59 wherein:
the server secret data includes a random integer b;
the server request data includes a value $M=w^a$, where
   $w=f$(user secret data), wherein f is a function which generates an element of a finite group G in which exponentiation is efficient but the discrete logarithm problem is computationally infeasible;
   a is an ephemeral client secret; and
   the exponentiation $w^a$ is computed in the group G; and
the step of computing the server response data includes computing a value $M^b$ wherein the exponentiation is computed in the group G.

61. The computer program product of claim 60 wherein the group G is selected from:
a multiplicative group of the set of integers modulo p, where p is a large prime suitable as a Diffie-Hellman modulus; and
a group of points on an elliptic curve over a finite field.

62. The computer program product of claim 59 wherein the server response data includes a nonce which distinguishes the server response data from other instances of server response data provided by the secret holding server for the user.

63. The computer program product of claim 59 wherein the method steps further comprise:
accessing verifier data, wherein the verifier data enables a verification server to verify that a device has successfully recovered the strong secret data;
receiving proof data from the device;
responsive to the verifier data and the proof data received from the device, determining whether the device has successfully regenerated the strong secret data; and
responsive to a determination that the device has not successfully recovered the strong secret data, updating a record of unsuccessful attempts to recover the strong secret data.

64. The computer program product of claim 63 wherein:
the verifier data includes public data which corresponds to a user's private data, wherein a first entity with access to the private data can prove said access to a second entity with access to the public data without disclosing the private data to the second entity; and
the step of determining whether the device has successfully recovered the strong secret data comprises determining whether the proof data proves that the device has access to the private data.

65. The computer program product of claim 64 wherein:
the step of determining whether the device has successfully recovered the strong secret data further comprises determining whether the proof data proves that the device has access to a nonce which confirms freshness of the proof data.

66. The computer program product of claim 65 wherein:
the user's private data includes a private key for use in a digital signature system;
the proof data includes digitally signed data which allegedly contains the nonce and allegedly has been digitally signed using the private key;
the step of determining whether the proof data proves that the device has access to the private data includes verifying that the digitally signed data has been digitally signed using the private key; and
the step of determining whether the proof data proves that the device has access to the nonce includes verifying that the digitally signed data contains the nonce or a value derived from the nonce.

67. The computer program product of claim 63 wherein:
the verifier data is a one-way function of the strong secret data; and
the step of determining whether the device has successfully recovered the strong secret data comprises determining whether the proof data proves that the device can compute the verifier data.

68. The computer program product of claim 67 wherein:
the step of determining whether the device has successfully recovered the strong secret data further comprises determining whether the proof data proves that the device has access to a nonce which confirms freshness of the proof data.

69. The computer program product of claim 68 wherein the step of determining whether the device has successfully recovered the strong secret data comprises:
computing an expected proof data as a one-way function of the verifier data and the nonce; and
comparing the expected proof data with the proof data received from the device.

70. The computer program product of claim 59 wherein the method steps further comprise:
accessing verifier data, wherein the verifier data enables a verification server to verify that a device has successfully recovered the strong secret data;
receiving proof data from the device, the proof data including a user-originated message to be digitally signed;
responsive to the verifier data and the proof data received from the device, determining whether the device has successfully regenerated the strong secret data; and
responsive to a determination that the device has successfully recovered the strong secret data, generating a digital signature component based on the user-originated message, wherein a digital signature of the user-originated message is a function of the digital signature components for at least two verification servers; and
transmitting the digital signature component to the device.

71. The computer program product of claim 59 wherein the method steps further comprise:
receiving token possession proof data for proving presence of a user's hardware token;
wherein the step of transmitting server response data to the device is responsive to a determination that the user's hardware token is present.

72. A computer program product having instructions executable by a generating client for instructing the generating client to perform method steps for enabling devices to securely regenerate a user's strong secret data from weak secret data for the user, the method steps comprising:

determining the user's weak secret data;

computing server request data for a secret holding server, wherein the server request data is a function of the weak secret data and, of an ephemeral client secret, and the server request data does not reveal information about the weak secret data without knowledge of the ephemeral client secret;

receiving server response data from the secret holding server, wherein the server response data is a function of the server secret data for the secret holding server and of the server request data, and the server response data does not reveal information about the server secret data without knowledge of the weak secret data and the ephemeral client secret;

computing a secret component for the secret holding server as a function of the server response data received from the secret holding server and of the ephemeral client secret, wherein the secret component is a function of the weak secret data and of the server secret data but is independent of the ephemeral client secret;

computing the user's strong secret data as a function of the secret component; and determining verifier data for at least one verification server, wherein the verifier data enables the verification server to verify that a device has successfully recovered the strong secret data but it is computationally infeasible for the verification server to determine the weak secret data based only on access to its verifier data.

73. The computer program product of claim 72 wherein:

the server secret data includes a random integer b;

the secret component is a value $K=h(w^b)$, wherein
h is a function;
w=f(weak secret data), wherein f is a function which generates an element of a finite group G in which exponentiation is efficient but the discrete logarithm problem is computationally infeasible; and
the exponentiation $w^b$ is computed in the group G;

the ephemeral client secret is a random integer a for which there exists a corresponding integer a' such that $x^{aa'}=x$ for all x in group G;

the server request data is computed as the value $M=w^a$ wherein the exponentiation is computed in the group G;

the server response data is computed as the value $c=M^b$ wherein the exponentiation is computed in the group G; and the secret component is computed as the value $K=h(c^{a'})$ wherein the exponentiation is computed in the group G.

74. The computer program product of claim 73 wherein the group G is selected from:

a multiplicative group of the set of integers modulo p, where p is a large prime suitable as a Diffie-Hellman modulus; and a group of points on an elliptic curve over a finite field.

75. The computer program product of claim 73 wherein the method steps further comprise:

encrypting private data for the user using the strong secret data as a cryptographic key in a symmetric cryptosystem; wherein the step of determining verifier data includes determining public data which corresponds to the user's private data, wherein a first entity with access to the private data can prove said access to a second entity with access to the public data without disclosing the private data to the second entity.

76. The computer program product of claim 72 wherein the step of determining verifier data comprises computing verifier data as a one-way function of the strong secret data.

77. A computer program product having instructions executable by a recovery client for instructing the recovery client to perform method steps for enabling devices to securely regenerate a user's strong secret data from weak secret data for the user, the method steps comprising:

receiving the user's weak secret data;

computing server request data for a secret holding server, wherein the server request data is a function of the weak secret data and of an ephemeral client secret, and the server request data does not reveal information about the weak secret data without knowledge of the ephemeral client secret;

receiving server response data from the secret holding server, wherein the server response data is a function of the server secret data for the secret holding server and of the server request data, and the server response data does not reveal information about the server secret data without knowledge of the weak secret data and the ephemeral client secret;

computing a secret component for the secret holding server as a function of the server response data received from the secret holding server and of the ephemeral client secret, wherein the secret component is a function of the weak secret data and of the server secret data but is independent of the ephemeral client secret;

computing the user's strong secret data as a function of the secret component;

determining proof data for proving to at least one verification server that the strong secret data was successfully computed; and transmitting the proof data to the verification servers.

78. The computer program product of claim 77 wherein:

the server secret data includes a random integer b; and the secret component is a value $K=h(w^b)$, wherein
h is a function;
w=f(weak secret data), wherein f is a function which generates an element of a finite group G in which exponentiation is efficient but the discrete logarithm problem is computationally infeasible; and
the exponentiation $w^b$ is computed in the group G;

the ephemeral client secret is a random integer a for which there exists a corresponding integer a' such that $x^{aa'}=x$ for all x in group G;

the server request data is computed as the value $M=w^a$ wherein the exponentiation is computed in the group G;

the server response data is computed as the value $c=M^b$ wherein the exponentiation is computed in the group G; and the secret component is computed as the value $K=h(c^{a'})$ wherein the exponentiation is computed in the group G.

79. The computer program product of claim 78 wherein the group G is selected from:

a multiplicative group of the set of integers modulo p, where p is a large prime suitable as a Diffie-Hellman modulus; and a group of points on an elliptic curve over a finite field.

80. The computer program product of claim 77 wherein the method steps further comprise:

obtaining encrypted private data for the user, wherein a first entity with access to the private data can prove said access to a second entity with access to corresponding public data without disclosing the private data to the second entity; and decrypting the encrypted private data using the strong secret data as a cryptographic key in a symmetric cryptosystem; wherein the step of determining proof data comprises computing proof data based on the decrypted private data.

81. The computer program product of claim 80 wherein the step of determining proof data comprises determining proof data as a function of a nonce which distinguishes the proof data from other instances of proof data provided for the user.

82. The computer program product of claim 81 wherein:

the user's private data includes a private key for use in a digital signature system; and the step of determining proof data comprises digitally signing a message containing the nonce using the private key.

83. The computer program product of claim 77 wherein the step of determining proof data comprises computing proof data as a one-way function of the strong secret data.

84. The computer program product of claim 83 wherein:

the step of determining proof data comprises determining the proof data as a function of a nonce which distinguishes the proof data from other instances of proof data provided for the user.

85. The computer program product of claim 84 wherein the step of determining proof data comprises:

computing verifier data as a one-way function of the strong secret data; and computing the proof data as a one-way function of the verifier data and of the nonce.

86. The computer program product of claim 77 wherein the method steps further comprise:

determining token possession proof data for proving presence of a user's hardware token; and transmitting the token possession proof data to at least one server selected from a group consisting of the secret holding servers and the verification servers.

87. A system for enabling devices to securely regenerate a user's strong secret data from weak secret data for the user, the system comprising:

a generating client and at least two secret holding servers coupled to the generating client, for executing the following method steps:

the generating client determining the user's weak secret data;

each secret holding server and the generating client computing secret components for each of at least two secret holding servers, wherein the secret component for each secret holding server is a function of the user's weak secret data and of server secret data for the secret holding server, said computing secret components includes, for at least one secret holding server:

the generating client computing and transmitting server request data to the secret holding server, wherein the server request data is a function of the weak secret data and of an ephemeral client secret, and the server request data does not reveal information about the weak secret data without knowledge of the ephemeral client secret, the secret holding server computing and transmitting server response data to the generating client, wherein the server response data is a function of the server secret data for the secret holding server and of the server request data, and the server response data does not reveal information about the server secret data without knowledge of the weak secret data and the ephemeral client secret, and the generating client computing the secret component for the secret holding server as a function of the server response data received from the secret holding server and of the ephemeral client secret, wherein the secret component is a function of the weak secret data and of the server secret data but is independent of the ephemeral client secret;

the generating client computing the user's strong secret data, wherein the strong secret data is a function of the secret components for the secret holding servers; and the generating client determining verifier data for each of at least two verification servers, wherein the verifier data for each verification server enables the verification server to verify that a device has successfully recovered the strong secret data but it is computationally infeasible for the verification server to determine the weak secret data based only on access to its verifier data.

88. The system of claim 87 wherein:

the server secret data for at least one secret holding server i includes a random integer b(i), where i is an index for the secret holding servers;

the step of computing the server request data for the secret holding server i comprises computing the value $M=w^a$ wherein w=f(weak secret data), wherein f is a function which generates an element of a finite group G in which exponentiation is efficient but the discrete logarithm problem is computationally infeasible; and the ephemeral client secret includes the random integer a for which there exists a corresponding integer a' such that $x^{aa'}=x$ for all x in the group G;

the step of receiving the server response data comprises receiving the value $c(i)=M^{b(i)}$ wherein the exponentiation is computed in the group G; and the step of computing the secret component comprises computing the value $K(i)=h(c(i)^{a'})$ wherein h is a function and the exponentiation is computed in the group G.

89. The system of claim 88 wherein the group G is selected from:

a multiplicative group of the set of integers modulo p, where p is a large prime suitable as a Diffie-Hellman modulus; and a group of points on an elliptic curve over a finite field.

90. A system for enabling devices to securely regenerate a user's strong secret data from weak secret data for the user, the system comprising:

a generating client and at least two secret holding servers coupled to the generating client, for executing the following method steps:

the generating client determining the user's weak secret data;

each secret holding server and the generating client computing secret components for each of at least two secret holding servers, wherein the secret component for each secret holding server is a function of the user's weak secret data and of server secret data for the secret holding server, said computing secret components includes, for at least one secret holding server:

the generating client encrypting private data for the user using the strong secret data as a cryptographic key in a symmetric cryptosystem; and the generating client determining verifier data for each of at least two verification servers, wherein the verifier data for each verification server enables the verification server to verify that a device has successfully recovered the strong secret data but it is computationally infeasible for the verification server to determine the weak secret data based only on access to its verifier data, said determining verifier data includes, for at least one verification server, determining public data which corresponds to the user's private data, wherein a first entity with access to the private data can prove said access to a second entity with access to the public data without disclosing the private data to the second entity.

91. A system for securely regenerating a user's strong secret data from weak secret data for the user, the system comprising:

a recovery client and at least two secret holding servers coupled to the recovery client, for executing the following method steps:

the recovery client receiving the user's weak secret data;

each secret holding server and the recovery client computing secret components for each of at least two secret holding servers, wherein the secret component for each secret holding server is a function of the user's weak secret data and of server secret data for the secret holding server, said computing secret components includes, for at least one secret holding server;

the recovery client computing and transmitting server request data to the secret holding server, wherein the server request data is a function of the weak secret data and of an ephemeral client secret, and the server request data does not reveal information about the weak secret data without knowledge of the ephemeral client secret, the secret holding server computing and transmitting server response data to the recovery client responsive to a determination that it is unlikely that a party without access to the weak secret data is attempting to regenerate the strong secret data, wherein the server response data is a function of the server secret data for the secret holding server and of the server request data, and the server response data does not reveal information about the server secret data without knowledge of the weak secret data and the ephemeral client secret, and the recovery client computing the secret component for the secret holding server as a function of the server response data received from the secret holding server and of the ephemeral client secret, wherein the secret component is a function of the weak secret data and of the server secret data but is independent of the ephemeral client secret;

the recovery client computing the user's strong secret data, wherein the strong secret data is a function of the secret components for the secret holding servers;

the recovery client determining proof data for proving to at least two verification servers that the strong secret data was successfully computed.

92. The system of claim 91 wherein:

the server secret data for at least one secret holding server i includes a random integer $b(i)$, where i is an index for the secret holding servers;

the step of computing the server request data for the secret holding server i comprises computing the value $M=w^a$ wherein $w=f(\text{weak secret data})$, wherein f is a function which generates an element of a finite group G in which exponentiation is efficient but the discrete logarithm problem is computationally infeasible; and the ephemeral client secret includes the random integer a for which there exists a corresponding integer a' such that $x^{aa'}=x$ for all x in the group G;

the step of computing the server response data comprises receiving the value $c(i)=M^{b(i)}$ wherein the exponentiation is computed in the group G; and the step of computing the secret component comprises computing the value $K(i)=h(c(i)^{a'})$ wherein h is a function and the exponentiation is computed in the group G.

93. The system of claim 92 wherein the group G is selected from:

a multiplicative group of the set of integers modulo p, where p is a large prime suitable as a Diffie-Hellman modulus; and a group of points on an elliptic curve over a finite field.

94. The system of claim 91 wherein the server response data includes a nonce which distinguishes the server response data from other instances of server response data provided by the secret holding server for the user.

95. A system for securely regenerating a user's strong secret data from weak secret data for the user, the system comprising:

a recovery client and at least two secret holding servers coupled to the recovery client, for executing the following method steps:

the recovery client receiving the user's weak secret data;

each secret holding server and the recovery client computing secret components for each of at least two secret holding servers, wherein the secret component for each secret holding server is a function of the user's weak secret data and of server secret data for the secret holding server;

the recovery client computing the user's strong secret data, wherein the strong secret data is a function of the secret components for the secret holding servers;

the recovery client determining proof data for proving to at least two verification servers that the strong secret data was successfully computed;

the recovery client obtaining encrypted private data for the user, wherein a first entity with access to the private data can prove said access to a second entity with access to corresponding public data without disclosing the private data to the second entity; and the recovery client decrypting the encrypted private data using the strong secret data as a cryptographic key in a symmetric cryptosystem; wherein the step of determining proof data for the verification servers comprises, for at least one verification server, determining proof data based on the decrypted private data.

96. A system for securely regenerating a user's strong secret data from weak secret data for the user, the system comprising:

a recovery client, at least two secret holding servers coupled to the recovery client and at least two verification servers coupled to the recovery client, for executing the following method steps:

the recovery client receiving the user's weak secret data;

each secret holding server and the recovery client computing secret components for each of at least two secret holding servers, wherein the secret component for each secret holding server is a function of the user's weak secret data and of server secret data for the secret holding server;

the recovery client computing the user's strong secret data, wherein the strong secret data is a function of the secret components for the secret holding servers;

the recovery client determining proof data for proving to the verification servers that the strong secret data was successfully computed;

the recovery client transmitting the proof data to the verification servers;

each verification server accessing verifier data, wherein the verifier data enables the verification server to verify that the recovery client has successfully recovered the strong secret data;

responsive to the verifier data and the proof data received from the recovery client, each verification server determining whether the recovery client has successfully recovered the strong secret data; and responsive to a determination that the recovery client has not successfully recovered the strong secret data, each verification server updating a record of unsuccessful attempts to recover the strong secret data.

97. The system of claim 96 wherein:

the verifier data includes public data which corresponds to a user's private data, wherein a first entity with access to the private data can prove said access to a second entity with access to the public data without disclosing the private data to the second entity; and the step of determining whether the recovery client has successfully recovered the strong secret data comprises determining whether the proof data proves that the recovery client has access to the private data.

98. The system of claim 97 wherein:

the step of determining whether the recovery client has successfully recovered the strong secret data further comprises determining whether the proof data proves that the recovery client has access to a nonce which confirms freshness of the proof data.

99. The system of claim 98 wherein:

the user's private data includes a private key for use in a digital signature system;

the proof data includes digitally signed data which allegedly contains the nonce and allegedly has been digitally signed using the private key;

the step of determining whether the proof data proves that the recovery client has access to the private data includes verifying that the digitally signed data has been digitally signed using the private key; and the step of determining whether the proof data proves that the recovery client has access to the nonce includes verifying that the digitally signed data contains the nonce or a value derived from the nonce.

100. The system of claim 96 wherein:

the verifier data is a one-way function of the strong secret data; and the step of determining whether the recovery client has successfully recovered the strong secret data comprises determining whether the proof data proves that the recovery client can compute the verifier data.

101. The system of claim 100 wherein:

the step of determining whether the recovery client has successfully recovered the strong secret data further comprises determining whether the proof data proves that the, recovery client has access to a nonce which confirms freshness of the proof data.

102. The system of claim 101 wherein the step of determining whether the recovery client has successfully recovered the strong secret data comprises:

computing an expected proof data as a one-way function of the verifier data and the nonce; and comparing the expected proof data with the proof data received from the recovery client.

103. A system for securely regenerating a user's strong secret data from weak secret data for the user, the system comprising:

a recovery client, at least two secret holding servers coupled to the recovery client and at least two verification servers coupled to the recovery client, for executing the following method steps:

the recovery client receiving the user's weak secret data;

each secret holding server and the recovery client computing secret components for each of at least two secret holding servers, wherein the secret component for each secret holding server is a function of the user's weak secret data and of server secret data for the secret holding server;

the recovery client computing the user's strong secret data, wherein the strong secret data is a function of the secret components for the secret holding servers;

the recovery client determining proof data for proving to the verification servers that the strong secret data was successfully computed;

the recovery client transmitting the proof data to the verification servers, the proof data including a user-originated message to be digitally signed;

each verification server accessing verifier data, wherein the verifier data enables the verification server to verify that a device has successfully recovered the strong secret data;

responsive to the verifier data and the proof data received from the recovery client, each verification server determining whether the recovery client has successfully regenerated the strong secret data; and responsive to a determination that the recovery client has successfully recovered the strong secret data, each verification server generating and transmitting to the recovery client a digital signature component based on the user-originated message; and the recovery client computing a digital signature of the user-originated message as a function of the digital signature components.

104. A system for securely regenerating a user's strong secret data from weak secret data for the user, the system comprising:

a recovery client and at least two secret holding servers coupled to the recovery client, for executing the following method steps:

the recovery client receiving the user's weak secret data;

each secret holding server and the recovery client computing secret components for each of at least two secret holding servers, wherein the secret component for each secret holding server is a function of the user's weak secret data and of server secret data for the secret holding server;

the recovery client computing the user's strong secret data, wherein the strong secret data is a function of the secret components for the secret holding servers;

the recovery client determining proof data for proving to at least two verification servers that the strong secret data was successfully computed;

the recovery client determining token possession proof data for proving presence of a user's hardware token; and the recovery client transmitting the token possession proof data to at least one server selected from a group consisting of the secret holding servers and the verification servers.

105. A system for securely regenerating a user's strong secret data from weak secret data for the user, the system comprising:

a recovery client and at least two secret holding servers coupled to the recovery client, for executing the following method steps:

the recovery client receiving the user's weak secret data;

each secret holding server and the recovery client computing secret components for each of at least two secret holding servers, wherein the secret component for each secret holding server is a function of the user's weak secret data and of server secret data for the secret holding server;

the recovery client computing the user's strong secret data, wherein the strong secret data is a function of the secret components for the secret holding servers;

the recovery client determining proof data for proving to at least two verification servers that the strong secret data was successfully computed, said determining proof data includes determining the proof data as a function of user data which the verification server can authenticate as originating from the user.

106. A system for enabling devices to securely regenerate a user's strong secret data from weak secret data for the user, the system comprising:

a generating client and at least one secret holding server coupled to the generating client, for executing the following method steps:

the generating client determining the user's weak secret data;

the generating client computing and transmitting server request data to the secret holding server, wherein the server request data is a function of the weak secret data and of an ephemeral client secret, and the server request data does not reveal information about the weak secret data without knowledge of the ephemeral client secret;

the secret holding server computing and transmitting server response data to the generating client, wherein the server response data is a function of the server secret data for the secret holding server and of the server request data, and the server response data does not reveal information about the server secret data without knowledge of the weak secret data and the ephemeral client secret;

the generating client computing a secret component for the secret holding server as a function of the server response data received from the secret holding server and of the ephemeral client secret, wherein the secret component is a function of the weak secret data and of the server secret data but is independent of the ephemeral client secret;

the generating client computing the user's strong secret data as a function of the secret component; and the generating client determining verifier data for at least one verification server, wherein the verifier data enables the verification server to verify that a device has successfully recovered the strong secret data but it is computationally infeasible for the verification server to determine the weak secret data based only on access to its verifier data.

107. The system of claim 106 wherein:

the server secret data includes a random integer b;

the secret component is a value $K=h(w^b)$, wherein
  h is a function;
  w=f(weak secret data), wherein f is a function which generates an element of a finite group G in which exponentiation is efficient but the discrete logarithm problem is computationally infeasible; and
  the exponentiation $w^b$ is computed in the group G;

the ephemeral client secret is a random integer a for which there exists a corresponding integer a' such that $x^{aa'}=x$ for all x in group G;

the server request data is computed as the value $M=w^a$ wherein the exponentiation is computed in the group G;

the server response data is computed as the value $c=M^b$ wherein the exponentiation is computed in the group G; and the secret component is computed as the value $K=h(c^{a'})$ wherein the exponentiation is computed in the group G.

108. The system of claim 107 wherein the group G is selected from:

a multiplicative group of the set of integers modulo p, where p is a large prime suitable as a Diffie-Hellman modulus; and a group of points on an elliptic curve over a finite field.

109. The system of claim 106 wherein the method steps further comprise:

the generating client encrypting private data for the user using the strong secret data as a cryptographic key in a symmetric cryptosystem; wherein the step of determining verifier data includes determining public data which corresponds to the user's private data, wherein a first entity with access to the private data can prove said access to a second entity with access to the public data without disclosing the private data to the second entity.

110. The system of claim 106 wherein the step of determining verifier data comprises computing verifier data as a one-way function of the strong secret data.

111. A system for securely regenerating a user's strong secret data from weak secret data for the user, the system comprising:

a recovery client and at least one secret holding server coupled to the recovery client, for executing the following method steps:

the recovery client receiving the user's weak secret data;

the recovery client computing and transmitting server request data to the secret holding server, wherein the server request data is a function of the weak secret data and of an ephemeral client secret, and the server request data does not reveal information about the weak secret data without knowledge of the ephemeral client secret;

the secret holding server computing and transmitting server response data to the recovery client, wherein the server response data is a function of the server secret data for the secret holding server and of the server request data, and the server response data does not reveal information about the server secret data without knowledge of the weak secret data and the ephemeral client secret;

the recovery client computing a secret component for the secret holding server as a function of the server response data received from the secret holding server and of the ephemeral client secret, wherein the secret component is a function of the weak secret data and of the server secret data but is independent of the ephemeral client secret;

the recovery client computing the user's strong secret data as a function of the secret component; and the recovery client determining proof data for proving to at least one verification server that the strong secret data was successfully computed.

112. The system of claim 111 wherein:

the server secret data includes a random integer b;

the secret component is a value $K=h(w^b)$, wherein
  h is a function;
  w=f(weak secret data), wherein f is a function which generates an element of a finite group G in which exponentiation is efficient but the discrete logarithm problem is computationally infeasible; and
  the exponentiation $w^b$ is computed in the group G;

the ephemeral client secret is a random integer a for which there exists a corresponding integer a' such that $x^{aa'}=x$ for all x in group G;

the server request data is computed as the value $M=w^a$ wherein the exponentiation is computed in the group G;

the server response data is computed as the value $c=M^b$ wherein the exponentiation is computed in the group G; and the secret component is computed as the value $K=h(c^{a'})$ wherein the exponentiation is computed in the group G.

113. The system of claim 112 wherein the group G is selected from:

a multiplicative group of the set of integers modulo p, where p is a large prime suitable as a Diffie-Hellman modulus; and a group of points on an elliptic curve over a finite field.

114. The system of claim 111 wherein the method steps further comprise:

the recovery client obtaining encrypted private data for the user, wherein a first entity with access to the private data can prove said access to a second entity with access to corresponding public data without disclosing the private data to the second entity; and the recovery client decrypting the encrypted private data using the strong secret data as a cryptographic key in a symmetric cryptosystem; wherein the step of determining proof data comprises computing proof data based on the decrypted private data.

115. The system of claim 114 wherein the step of determining proof data comprises determining proof data as a function of a nonce which distinguishes the proof data from other instances of proof data provided for the user.

116. The system of claim 115 wherein:

the user's private data includes a private key for use in a digital signature system; and the step of determining proof data comprises digitally signing a message containing the nonce using the private key.

117. The system of claim 111 wherein the step of determining proof data comprises computing proof data as a one-way function of the strong secret data.

118. The system of claim 117 wherein:

the step of determining proof data comprises determining the proof data as a function of a nonce which distinguishes the proof data from other instances of proof data provided for the user.

119. The system of claim 118 wherein the step of determining proof data comprises:

computing verifier data as a one-way function of the strong secret data; and computing the proof data as a one-way function of the verifier data and of the nonce.

120. The system of claim 111 wherein the method steps further comprise:

the recovery client determining token possession proof data for proving presence of a user's hardware token; and the recovery client transmitting the token possession proof data to at least one server selected from a group consisting of the secret holding servers and the verification servers.

* * * * *

UNITED STATES PATENT AND TRADEMARK OFFICE
CERTIFICATE OF CORRECTION

PATENT NO. : 6,829,356 B1
DATED : December 7, 2004
INVENTOR(S) : Warwick S. Ford It is certified that error appears in the above-identified patent and that said Letters Patent is hereby corrected as shown below:

Title page,
Item [75], Inventor, change "Warwick S. Ford" to -- Warwick S. Ford --.
Item [56], References Cited, OTHER PUBLICATIONS,"Lomas, T.M.A., Gong L.; Saltzer, J.H., and Needham," reference, change "$12^{th}$ ACM Symposium on Operating System Principles," to -- $12^{th}$ *ACM Symposium on Operating System Principles*, --. change "*group*" Attacks on the Diffie-Hellman Key Agreement for S/MIME" to
-- *group" Attacks on the Diffie-Hellman Key Agreement for S/MIME* --.

Column 4,
Line 58, change "such a the" to -- such as the --.

Column 14,
Line 6, change "genera ting" to -- generating --.

Column 26,
Line 3, change "cryptosystern" to -- cryptosystem --.

Column 35,
Line 5, change "cryptosystern" to -- cryptosystem --.

Column 44,
Line 5, change "cryptosystern" to -- cryptosystem --.

Signed and Sealed this

Twenty-first Day of June, 2005

JON W. DUDAS
*Director of the United States Patent and Trademark Office*